US006979693B2

(12) United States Patent
Goldstein et al.

(10) Patent No.: US 6,979,693 B2
(45) Date of Patent: *Dec. 27, 2005

(54) PYRAZOLE DERIVATIVES-P38 MAP KINASE INHIBITORS

(75) Inventors: David Michael Goldstein, San Jose, CA (US); Sharada Shenvi Labadie, Sunnyvale, CA (US); David Mark Rotstein, Sunnyvale, CA (US); Eric Brian Sjogren, Mountain View, CA (US); Francisco Xavier Talamas, Mountain View, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/066,040

(22) Filed: Feb. 1, 2002

(65) Prior Publication Data

US 2003/0018051 A1 Jan. 23, 2003

Related U.S. Application Data

(63) Continuation of application No. 09/305,737, filed on May 5, 1999, now Pat. No. 6,376,527.
(60) Provisional application No. 60/130,369, filed on Apr. 21, 1999, provisional application No. 60/122,410, filed on Feb. 2, 1999, and provisional application No. 60/084,250, filed on May 5, 1998.

(51) Int. Cl.⁷ .................. A61K 31/415; A61K 31/4155; C07D 401/06; C07D 231/38
(52) U.S. Cl. .................... 514/341; 514/404; 546/275.4; 548/372.5
(58) Field of Search .................. 548/372.5; 546/275.4; 514/341, 404

(56) References Cited

U.S. PATENT DOCUMENTS

| 5,256,634 A | 10/1993 | Schallnor et al. | |
| 5,712,303 A | 1/1998 | Faraci et al. | |
| 6,376,527 B1 * | 4/2002 | Goldstein et al. | 514/404 |

FOREIGN PATENT DOCUMENTS

| DE | 19518054 A1 | 9/1996 | |
| EP | 0 129 846 B1 | 1/1985 | |
| FR | 2100973 | 3/1972 | |
| JP | 4731979 | 11/1972 | |
| WO | WO-94/13643 A1 * | 6/1994 | ......... C07D/231/44 |
| WO | WO 96/10568 | 4/1996 | |

OTHER PUBLICATIONS

Tupper, et al., *Synthesis*, vol. 3: pp 337–341 (1997) "Steric and electronic control in the addition of hydrazine and phenylhydrazine to α–[(dimethylamino)methylene] β–oxoarylpropanenitriles".

Rudorf, et al., *J. Prakt. Chem.*, vol. 320:4, pp 585–599 (1978) "Acylketen–S,S–und Acylketen–S,N–acetale als Bausteine fur Heterocyclen: Pyrazole und Isoxazole".

Butler, et al., *J. Med. Chem.*, vol. 27: pp 1396–1400 (1984) "(1,3–Dialkyl–5–amino–1H–pyrazol–4–yl)arylmethanones. A Series of Novel Central Nervous System Depressants".

Nishiwaki, et al., *J. Chem. Soc., Perkin Trans I.*, vol. 15, pp 1871–1875 (1974) "Studies on Heterocyclic Chemistry. Part XIX. Synthesis of 4–Aroyl–1–arylpyrazoles from α Aroyl–β–anilinoacrylonitriles and Photochemistry of 4–Carbonyl–substituted Pyrazoles".

* cited by examiner

*Primary Examiner*—Laura L. Stockton
(74) *Attorney, Agent, or Firm*—Robert C. Hall

(57) ABSTRACT

The present invention relates to certain pyrazole derivatives of Formula (I):

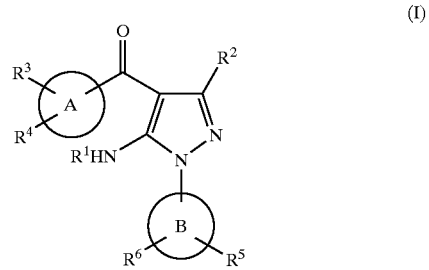

that are p-38 MAP kinase inhibitors, pharmaceutical compositions containing them, methods for their use, and methods for preparing these compounds.

19 Claims, No Drawings

PYRAZOLE DERIVATIVES-P38 MAP KINASE INHIBITORS

CROSS-REFERENCE TO RELATED APPLICATIONS

This application is a continuation application of U.S. application Ser. No. 09/305,737, filed May 5, 1999, now U.S. Pat. No. 6,376,527 and claims the benefit under 35 U.S.C. 119 (e) of U.S. Provisional application Ser. No. 60/084,250, filed May 5, 1998, U.S. Provisional Application Ser. No. 60/122,410, filed Feb. 2, 1999, and U.S. Provisional Application Ser. No. 60/130,360, filed Apr. 21, 1999, all of which are incorporated herein by reference in their entirety.

FIELD OF THE INVENTION

This invention relates to certain pyrazole derivatives that inhibit p38 MAP kinase, pharmaceutical compositions containing them, methods for their use, and methods for preparing these compounds.

BACKGROUND INFORMATION AND RELATED DISCLOSURES

TNF and IL-1 have been shown to be central players in the pathological processes underlying many chronic inflammatory and autoimmune diseases. IL-1 is implicated in mediating or exacerbating diseases such as rheumatoid arthritis (see., Arend, W. P. *Arthritis & Rheumatism* 38(2): 151–160, (1995)), osteoarthritis, bone resorption, toxic shock syndrome, tuberculosis, atherosclerosis, diabetes, Hodgkin's disease (see., Benharroch, D.; et. al. *Euro. Cytokine Network* 7(1):51–57) and Alzheimer's disease. Excessive or unregulated TNF production has been implicated in mediating or exacerbating diseases such as rheumatoid arthritis ((see., Maini, R. N.; et. al.*APMIS.* 105(4): 257–263, (1997); Feldmann, M.,*J. of the Royal College of Physicians of London* 30(6): 560–570, (1996); Lorenz, H. M.; et al.,*J. of Immunology* 156(4): 1646–1653, (1996)) osteoarthritis, spondylitis, sepsis, septic shock ((see., Abraham, E.; et al. *JAMA,* 277(19):1531–1538, (1997), adult respiratory distress syndrome, asthma ((see., Shah, A.; et al. *Clin. & Exp. Allergy* 1038–1044, (1995) and Lassalle, P., et al. *Clin. & Esp. Immunol.* 94(1): 105–110, (1993)), bone resorption diseases, fever ((see., Cooper, Al. L., et al. *Am. J. of Physiology* 267(6 Pt. 2): 1431–1436)), encephalomyelitis, demyellination ((see., Klindert, W. E.; et al. *J. of Neuroimmunol.* 72(2): 163–168, (1997)) and periodontal diseases.

Clinical trials with IL-1 and TNF receptor antagonists have shown that blocking the ability of these cytokines to signal through their receptors leads to significant improvement, in humans, in inflammatory diseases. Therefore, modulation of these inflammatory cytokines is considered one of the most effective strategies to block chronic inflammation and have positive therapeutic outcomes. It has also been shown that p38 MAP-kinase plays an important role in the translational control of TNF and IL-1 and is also involved in the biochemical signaling of these molecules ((see., Lee, J. C., et al. *Nature,* 372 (6508): 739–46, (1994)). Compounds that bind to p38 MAP are effective in inhibiting bone resorption, inflammation, and other immune and inflammation-based pathologies. The characterization of the p38 MAP kinase and its central role in the biosynthesis of TNF and IL-1 have made this kinase an attractive target for the treatment of diseases mediated by these cytokines.

It would therefore be desirable to provide p38 MAP kinase inhibitors and thereby provide a means of combating diseases mediated by pro-inflammatory cytokines such as TNF and IL-1. This invention fulfills this and related needs.

SUMMARY OF THE INVENTION

In a first aspect, this invention provides compounds selected from the group of compounds represented by Formula (I):

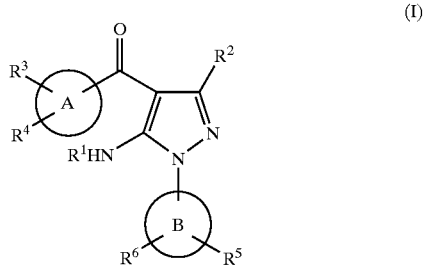

wherein:
R$^1$ is hydrogen or acyl;
R$^2$ is hydrogen or alkyl;
A is an aryl or heteroaryl ring;
B is an aryl or heteroaryl ring;
R$^3$ is selected from the group consisting of:
(a) amino, alkylamino or dialkylamino;
(b) acylamino;
(c) optionally substituted heterocyclyl;
(d) optionally substituted aryl or heteroaryl;
(e) heteroalkyl;
(f) heteroalkenyl;
(g) heteroalkynyl;
(h) heteroalkoxy;
(i) heteroalkylamino;
(j) optionally substituted heterocyclylalkyl;
(k) optionally substituted heterocyclylalkenyl;
(l) optionally substituted heterocyclylalkynyl;
(m) optionally substituted heterocyclylalkoxy, cyclyloxy or heterocyclyloxy;
(n) optionally substituted heterocyclylalkylamino;
(o) optionally substituted heterocyclylalkylcarbonyl;
(p) heteroalkylcarbonyl;
(q) —NHSO$_2$R$^6$ where R$^6$ is alkyl, heteroalkyl or optionally substituted heterocyclylalkyl;
(r) —NHSO$_2$NR$^7$R$^8$ where R$^7$ and R$^8$ are, independently of each other, hydrogen, alkyl or heteroalkyl;
(s) —Y—(alkylene)—R$^9$ where:
Y is a single bond, —O—, —NH— or —S(O)$_n$— (where n is an integer from 0 to 2); and
R$^9$ is cyano, optionally substituted heteroaryl, —COOH, —COR$^{10}$, —COOR$^{11}$, —CONR$^{12}$R$^{13}$, —SO$_2$R$^{14}$, —SO$_2$NR$^{15}$R$^{16}$, —NHSO$_2$R$^{17}$ or —NHSO$_2$NR$^{18}$R$^{19}$, where R$^{10}$ is alkyl or optionally substituted heterocycle, R$^{11}$ is alkyl, and R$^{12}$, R$^{13}$, R$^{14}$, R$^{15}$, R$^{16}$, R$^{17}$, R$^{18}$ and R$^{19}$ are, independently of each other, hydrogen, alkyl or heteroalkyl;
(t) —C(=NR$^{20}$)(NR$^{21}$R$^{22}$) were R$^{20}$, R$^{21}$ and R$^{22}$ independently represent hydrogen, alkyl or hydroxy, or R$^{20}$ and R$^{21}$ together are —(CH$_2$)$_n$— where n is 2 or 3 and R$^{22}$ is hydrogen or alkyl;
(u) —NHC(X)NR$^{23}$R$^{24}$ where X is —O— or —S—, and R$^{23}$ and R$^{24}$ are, independently of each other, hydrogen, alkyl or heteroalkyl;
(v) —CONR$^{25}$R$^{26}$ where R$^{25}$ and R$^{26}$ independently represent hydrogen, alkyl, heteroalkyl or optionally substituted heterocyclylalkyl, or $R^{25}$ and $R^{26}$ together with the nitrogen to which they are attached form an optionally substituted heterocyclyl ring;

(w) —S(O)$_n$R$^{27}$ where n is an integer from 0 to 2, and $R^{27}$ is alkyl, heteroalkyl, optionally substituted heterocyclylalkyl or —NR$^{28}$R$^{29}$ where $R^{28}$ and $R^{29}$ are, independently of each other, hydrogen, alkyl or heteroalkyl;

(x) cycloalkylalkyl, cycloalkylalknyl and cycloalkylalkynyl, all optionally substituted with alkyl, halo, hydroxy or amino;

(y) arylaminoalkylene or heteroarylaminoalkylene;

(z) Z-alkylene-NR$^{30}$R$^{31}$ or Z-alkylene-OR$^{32}$ where Z is —NH—, —N(alkyl)— or —O—, and $R^{30}$, $R^{31}$ and $R^{32}$ are independently of each other, hydrogen, alkyl or heteroalkyl;

(aa) —OC(O)-alkylene-CO$_2$H or —OC(O)—NR'R" (where R' and R" are independently hydrogen or alkyl); and (bb) heteroarylalkenylene or heteroarylalkynylene;

$R^4$ is selected from the group consisting of:
(a) hydrogen;
(b) halo;
(c) alkyl;
(d) alkoxy; and
(e) hydroxy;

$R^5$ is selected from the group consisting of:
(a) hydrogen;
(b) halo;
(c) alkyl;
(d) haloalkyl;
(e) thioalkyl;
(f) hydroxy;
(g) amino;
(h) alkylamino;
(i) dialkylamino;
(j) heteroalkyl;
(k) optionally substituted heterocycle;
(l) optionally substituted heterocyclylalkyl;
(m) optionally substituted heterocyclylalkoxy;
(n) alkylsulfonyl;
(o) aminosulfonyl, mono-alkylaminosulfonyl or dialkylaminosulfonyl;
(p) heteroalkoxy; and
(q) carboxy;

$R^6$ is selected from a group consisting of:
(a) hydrogen;
(b) halo;
(c) alkyl; and
(d) alkoxy; prodrugs, individual isomers, mixtures of isomers and pharmaceutically acceptable salts thereof.

In a second aspect, this invention provides pharmaceutical compositions containing a therapeutically effective amount of a compound of Formula (I) or its pharmaceutically acceptable salt and a pharmaceutically acceptable excipient.

In a third aspect, this invention provides a method of treatment of a disease in a mammal treatable by administration of a p38 MAP kinase inhibitor, comprising administration of a therapeutically effective amount of a compound of Formula (I) or its pharmaceutically acceptable salt.

In a fourth aspect, this invention provides processes for preparing compounds of Formula (I).

DETAILED DESCRIPTION OF THE INVENTION

DEFINITIONS

Unless otherwise stated, the following terms used in the specification and claims have the meanings given below:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, pentyl, and the like.

"Alkylene" means a linear saturated divalent hydrocarbon radical of one to six carbon atoms or a branched saturated divalent hydrocarbon radical of three to six carbon atoms, e.g., methylene, ethylene, propylene, 2-methylpropylene, pentylene, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkenylene" means a linear divalent hydrocarbon radical of two to six carbon atoms or a branched divalent hydrocarbon radical of three to six carbon atoms, containing at least one double bond, e.g., ethenylene, propenylene, and the like.

"Alkynyl" means a linear monovalent hydrocarbon radical of two to six carbon atoms or a branched divalent hydrocarbon radical of three to six carbon atoms, containing at least one triple bond, e.g., ethynyl, propynyl, and the like.

"Alkynylene" means a linear divalent hydrocarbon radical of two to six carbon atoms or a branched monovalent hydrocarbon radical of three to six carbon atoms, containing at least one triple bond, e.g., ethynylene, propynylene, and the like.

"Alkoxy" means a radical —OR where R is alkyl as defined above, e.g., methoxy, ethoxy, propoxy, 2-propoxy, the like.

"Acyl" means a radical —C(O)R where R is alkyl or haloalkyl e.g., acetyl, trifluoroacetyl, and the like.

"Acylamino" means a radical —NRC(O)R' where R is hydrogen or alkyl, and R' is alkyl, heteroalkyl or optionally substituted heterocyclylalkyl, e.g., acetylamino, 2-amino-2-methylpropionamide, and the like.

"Halo" means fluoro, chloro, bromo, or iodo, preferably fluoro and chloro.

"Haloalkyl" means alkyl substituted with one or more same or different halo atoms, e.g., —CH$_2$Cl, —CF$_3$, —CH$_2$CF$_3$, —CH$_2$CCl$_3$, and the like.

"Aryl" means a monovalent monocyclic or bicyclic aromatic hydrocarbon radical of 6 to 10 ring atoms e.g., phenyl, 1-naphthyl, 2-naphthyl, and the like. The aryl ring may optionally be fused to a 5-, 6- or 7-membered monocyclic saturated ring optionally containing 1 to 2 heteroatoms independently selected from oxygen, nitrogen or sulfur, the remaining ring atoms being C where one or two C atoms are optionally replaced by a carbonyl group. Representative aryl radicals with fused rings include, but are not limited to, 2,3-dihydrobenzo[1,4]dioxan, chroman, isochroman, 2,3-dihydrobenzofuran, 1,3-dihydroisobenzofuran, benzo[1,3]dioxole, 1,2,3,4-tetrahydroisoquinoline, 1,2,3,4-tetrahydroquinoline, 2,3-dihydro-1H-indole, 2,3-dihydro-1H-isoindole, benzimidazol-2-one, 3H-benzoxazol-2-one, and the like.

"Heteroaryl" means a monovalent monocyclic or bicyclic aromatic radical of 5 to 10 ring atoms containing one, two, or three ring heteroatoms selected from N, O, or S, the remaining ring atoms being C. The term also includes those radicals where a heteroatom within the ring has been oxidized or quaternized, such as, for example, to form an N-oxide or a quaternary salt. Representative examples include, but are not limited to, thienyl, benzothienyl, pyridyl, pyrazinyl, pyrimidinyl, pyridazinyl, quinolinyl, quinoxalinyl, imidazolyl, furanyl, benzofuranyl, thiazolyl, isoxazolyl, benzisoxazoyl, benzimidazolyl, triazolyl, pyrazolyl, pyrrolyl, indolyl, 2-pyridonyl, 4-pyridonyl, N-alkyl-2-pyridonyl, pyrazinonyl, pyridazinonyl, pyrimidinonyl, oxazolonyl, and their corresponding N-oxides, (e.g. pyridyl N-oxide, quinolinyl N-oxide), their quaternary salts and the like.

"Heterocycle" or "heterocyclyl" means a cyclic nonaromatic radical of 3 to 8 ring atoms in which one or two ring atoms are heteroatoms selected from N, O, or $S(O)_n$ (where n is an integer from 0 to 2), the remaining ring atoms being C where one or two C atoms are optionally replaced by a carbonyl group. The term also includes those radicals where a ring nitrogen atom has been oxidized or quaternized, such as, for example, to form an N-oxide or a quaternary salt. Representative examples include, but are not limited to, tetrahydropyranyl, tetrahydrofuranyl, tetrahydrothiophenyl, piperidino, morpholino, piperazino, pyrrolidino, oxiranyl, dioxane, 1,3-dioxolanyl, 2,2-dimethyl-1,3-dioxalanyl, sulfolanyl, 2-oxazolidonyl, 2-imidazolidonyl, S,S-dioxothiomorpholino, and the like.

"Heterocyclamino" means a saturated monovalent cyclic group of 4 to 8 ring atoms, wherein at least one ring atom is N and optionally contains one additional ring atom selected from N or O, the remaining ring atoms being C. The term includes groups such as pyrrolidino, piperidino, morpholino, piperazino and the like.

"Optionally substituted aryl, heteroaryl or heterocyclyl" means an aryl, heteroaryl or heterocyclyl ring as defined above, which is optionally substituted independently with one or two substituents selected from alkyl, phenyl, benzyl, haloalkyl, heteroalkyl, halo, cyano, acyl, —OR (where R is hydrogen or alkyl), —NRR' (where R and R' are independently selected from hydrogen, alkyl or acyl), —NHCOR (where R is alkyl), —$NRS(O)_nR'$ (where R is hydrogen or alkyl, n is an integer from 0 to 2 and R' is hydrogen, alkyl or heteroalkyl), —$NRS(O)_nNR'R''$ (where R is hydrogen or alkyl, n is an integer from 0 to 2 and R' and R'' are independently hydrogen, alkyl or heteroalkyl), —$S(O)_nR$ (where n is an integer from 0 to 2 and R is hydrogen, alkyl or heteroalkyl), —$S(O)_nNRR'$ (where n is an integer from 0 to 2 and R and R' are independently hydrogen, alkyl or heteroalkyl), —COOR, —(alkylene)COOR (where R is hydrogen or alkyl), —CONR'R'' or —(alkylene)CONR'R'' (where R' and R'' are independently hydrogen or alkyl).

"Heteroalkyl" means an alkyl radical as defined above, carrying one, two or three substituents selected from —$NR^aR^b$, —$OR^c$ wherein $R^a$, $R^b$ and $R^c$ are independently of each other hydrogen, alkyl or acyl, or $R^a$ and $R^b$ together form heterocycloamino group. Representative examples include, but are not limited to, hydroxymethyl, acetoxymethyl, 3-hydroxypropyl, 1,2-dihydroxyethyl, 2-methoxyethyl, 2-aminoethyl, 2-dimethylaminoethyl, 2-acetylaminoethyl, 3-[pyrrolidin-1-yl]ethyl and the like.

"Heteroalkenyl" means an alkenyl radical as defined above, carrying one or two substituents selected from —$NR^aR^b$, —$OR^c$ or —$S(O)_nR^d$ wherein $R^a$, $R^b$ and $R^c$ are independently of each other hydrogen or alkyl, and $R^d$ is alkyl or —NRR' (where R and R' are independently of each other hydrogen or alkyl. Representative examples include, but are not limited to, 3-hydroxy-1-propenyl, 3-aminoprop-1-enyl, 2-aminosulfonylethenyl, 2-methylsulfonylethenyl, and the like.

"Heteroalkynyl" means an alkynyl radical as defined above, carrying one or two substituents selected —$NR^aR^b$, —$OR^c$, —$S(O)_nR^d$ or —$S(O)_nNRR'$ (where R and R' are independently of each other hydrogen or alkyl) wherein $R^a$, $R^b$ and $R^c$ are independently of each other hydrogen or alkyl, and $R^d$ is alkyl and n is an integer from zero to two. Representative examples include, but are not limited to, 3-hydroxy-1-propynyl, 3-dimethylaminoprop-1-ynyl and the like.

"Heteroalkoxy" means a radical —OR where R is heteroalkyl group as defined above, e.g., 2-hydroxyethoxy, 3-hydroxypropoxy, 2,3-dihydroxypropoxy, 2-(1,3-dihydroxy)propoxy, 2-aminoethoxy, and the like.

"Heteroalkylamino" means a radical —$NR^aR^b$ where $R^a$ is hydrogen or alkyl, and $R^b$ is a heteroalkyl group as defined above, e.g., 2-hydroxyethylamino, 3-dimethylaminopropylamino, and the like.

"Optionally substituted heterocyclalkyl" means a radical —$R^aR^b$ where $R^a$ is an alkylene group, and $R^b$ is an optionally substituted heterocyclyl group as defined above e.g., 2-(morpholin-4-yl)ethyl, 3-(piperidin-1-yl)-2-methylpropyl, and the like.

"Optionally substituted heterocyclylalkenyl" means a radical —$R^aR^b$ where $R^a$ is an alkenylene group and $R^b$ is an optionally substituted heterocyclyl group as defined above e.g., 3-(morpholin-4-yl)prop-1-yl)prop-1-ethyll, 3-(piperidin-1-yl)prop-1-enyl, 3-(4-methylpiperazin-1-yl) prop-1-enyl, and the like.

"Optionally substituted heterocyclylalkynyl" means a radical —$R^aR^b$ where $R^a$ is an alkynyl group and $R^b$ is an optionally substituted heterocyclyl group as defined above e.g., 3-(morpholin-4-yl)prop-1-ynyl, 3-(piperidin-1-yl) lprop-1-ynyl, and the like.

"Optionally substituted heterocyclylalkoxy" means a radical —OR where R is an optionally substituted heterocyclylalkyl group as defined above, e.g., 2-(morpholin-4-yl)-ethoxy, 3-(piperazin-1-yl)propoxy, 2-[2-oxopyrrolidin-1-yl]ethoxy, and the like.

"Optionally substituted heterocyclylalkylamino" means a radical —$NR^aR^b$ where $R^a$ is hydrogen or alkyl and $R^b$ is an optionally substituted heterocyclylalkyl group as defined above, e.g., 2-(pyrrolidin-2-yl)ethylamino, 3-(piperidin-1-yl)propylamino, and the like.

"Optionally substituted heteroaralkyloxy means a radical —O—$R^a$ where $R^a$ is a heteroaralkyl radical e.g. 2-(pyridin-3-yl)ethoxy, 2-[3(2H)-pyridazon-1-yl]ethoxy and the like.

"Optional" or "optionally" means that the subsequently described event or circumstance may but need not occur, and that the description includes instances where the event or circumstance occurs and instances in which it does not. For example, "aryl group optionally mono- or di-substituted with an alkyl group" means that the alkyl may but need not be present, and the description includes situations where the aryl group is mono- or disubstituted with an alkyl group and situations where the heterocyclo group is not substituted with the alkyl group.

"Amino protecting group" refers to those organic groups intended to protect nitrogen atoms against undesirable reactions during synthetic procedures e.g., benzyl, benzyloxycarbonyl (CBZ), tert-butoxycarbonyl (Boc), trifluoroacetyl, and the like.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures; racemic or otherwise, thereof. The methods for the determination of stereochemistry and the separation of stereoisomers are well-known in the art (see discussion in Chapter 4 of "Advanced Organic Chemistry", 4th edition, J. March, John Wiley and Sons, New York, 1992).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. "A pharmaceutically acceptable excipient" as used in the specification and claims includes both one and more one such excipient.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 4,4'-methylenebis-(2-hydroxy-2-ene-1-carboxylic acid), 3-phenylpropionic acid, trimethylacetic acid, tertiary butylacetic acid, lauryl sulfuric acid, gluconic acid; glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Pro-drugs" means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy, amino, or sulfhydryl group in compound (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of Formula (I), and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

NOMENCLATURE

The naming and numbering of the compounds of this invention is illustrated below.

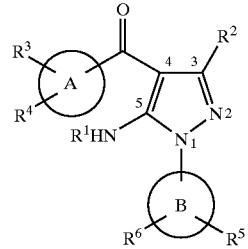

(I)

The nomenclature used in this application is generally based on the IUPAC recommendations, e.g., a compound of formula (I):

where $R^1$, $R^2$, $R^4$, $R^6$ are hydrogen,

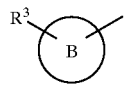

is 4-(3-hydroxypropyl)phenyl and

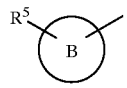

is 4-fluorophenyl is named 5-amino-1-(4-fluorophenyl)-4-[4-(3-hydroxypropyl)benzoyl]pyrazole.

where $R^1$, $R^2$, $R^4$, $R^6$ are hydrogen,

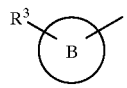

is 3-[3-(morpholin-4-yl)prop-1-ynyl]-phenyl and

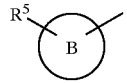

is 4-fluorophenyl is named 5-amino-1-(4-fluorophenyl)-4-[3-(3-morpholin-4-ylprop-1-ynyl)benzoyl]pyrazole.

Representative Compounds of this Invention are as Follows:

I. Compounds of Formula (I) where $R^1$, $R^2$ and $R^4$ are hydrogen, B is phenyl and the other groups are as defined below are:

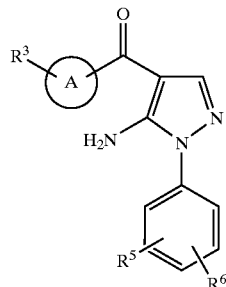

| CPD # | R³ⒶⲦ | R⁵ | R⁶ | M. Pt. ° C. | Mass Spec. (M⁺) |
|---|---|---|---|---|---|
| 1 | 4-(3-hydroxypropyl)phenyl | H | H | 148–152.5 | |
| 2 | 4-[3-(morpholin-4-yl)prop-1-enyl]phenyl | 4-F | H | 166.7–168.2 | |
| 3 | 3-[3-(morpholin-4-yl)prop-1-ynyl]phenyl | 4-F | H | 145.2–145.8 | |
| 4 | 3-[3-(morpholin-4-yl)prop-1-enyl]phenyl | 4-F | H | 161.6–162.8 | |
| 5 | 4-[3-(morpholin-4-yl)propyl]phenyl | 4-F.HCl | H | | 408 |
| 6 | 3-[3-(morpholin-4-yl)propyl]phenyl | 4-F.HCl | H | 211.9–212.6 | |
| 7 | 3-(3-hydroxyprop-1-ynyl)phenyl | 4-F | H | 219.2–219.6 | |
| 8 | 3-[3-(4-methylpiperazin-1-yl)prop-1-ynyl]phenyl | 4-F.2HCl | H | 270.8–271.1 | |
| 9 | 3-[3-(piperidin-1-yl)prop-1-ynyl]phenyl | 4-F.HCl | H | 205.3–207.4 | |
| 10 | 3-(2-aminosulfonylethenyl)phenyl | 4-F | H | | 370 |
| 11 | 3-cyanomethyloxyphenyl | 4-F | H | | |
| 12 | 3-[3-dimethylaminoprop-1-ynyl)]phenyl | 4-F.HCl | H | 229.9–230 | |
| 13 | 3-[2-(morpholin-4-yl)ethoxy]phenyl | 4-F | H | | |
| 14 | 3-[2-(morpholin-4-yl)ethoxy]phenyl | 4-F.HCl | H | 191.6–192.5 | |
| 15 | 3-[2-(morpholin-4-yl)ethoxy]phenyl | 2-F | 4-F | | 428 |
| 16 | 3-(3-methylaminoprop-1-ynyl)phenyl | 4-F | H | 210.6–210.8 | |
| 17 | 3-(4-methylpiperazin-1-yl)phenyl | 2-F.HCl | H | 142.5–151 | |
| 18 | 3-(morpholin-4-ylmethylcarbonyl)phenyl | 4-F.HCl | H | 227–231.8 | 408 |
| 19 | 3-(formamidoxime)phenyl | 4-F | H | 222.4–223.0 | |
| 20 | 3-(pyridin-3-yl)phenyl | 4-F | H | | |
| 21 | 3-[3-(piperidin-1-yl)propoxy]phenyl | 4-F | H | | 422 |
| 22 | 3-[2-(piperidin-1-yl)ethoxy]phenyl | 4-F | H | | 408 |
| 23 | 3-[3-(morpholin-4-yl)propoxy]phenyl | 4-F | H | | 424 |
| 24 | 3-[3-(4-methylpiperazin-1-yl)propoxy]phenyl | 4-F | H | | 437 |
| 25 | 3-[3-(2-hydroxymethylpyrrolidin-1-yl)propoxy]-phenyl | 4-F | H | | 438 |
| 26 | 3-[3-(2-aminocarbonylpyrrolidin-1-yl)propoxy]-phenyl | 4-F | H | | |
| 27 | 3-(3-cyanopropoxy)phenyl | 4-F | H | | 364 |
| 28 | 3-(diethylaminopropoxy)phenyl | 4-F | H | | 410 |
| 29 | 2-[3-(4-methylpiperazin-1-yl)propoxy]phenyl | 4-F | H | | 437 |
| 30 | 3-[3-(4-methylpiperazin-1-yl)propyl]phenyl | 4-F.2HCl | H | 254.5–254.9 | |
| 31 | 3-[3-(4-methylpiperazin-1-yl)ethyl]phenyl | 4-F.2HCl | H | 272.9–273.9 | |
| 32 | 3-[3-(piperidin-1-yl)propyl]phenyl | 4-F.HCl | H | 227.1–277.7 | |
| 33 | 3-(4-benzylpiperidin-1-yl)phenyl | 4-F | H | 156.2–160.9 | |
| 34 | 3-(methylaminocarbonylmethyloxy)phenyl | 4-F | H | 195.6–196.3 | |
| 35 | 3-(morpholin-4-ylcarbonylmethyloxy)phenyl | 4-F | H | 124.3–126.6 | |
| 36 | 3-(piperidin-1-ylcarbonylmethyloxy)phenyl | 4-F | H | | 422 |
| 37 | 3-(diethylaminocarbonylmethyloxy)phenyl | 4-F | H | | 410 |
| 38 | 3-(4-methylpiperazin-1-ylcarbonylmethyloxy)phenyl | 4-F | H | | 437 |
| 39 | 3-(2-dimethylaminoethoxy)phenyl | 4-F | H | | 368 |
| 40 | 3-(methylcarbonylmethyloxy)phenyl | 4-F | H | | 353 |
| 41 | 3-[4-(2-hydroxyethyl)piperazin-1-ylcarbonylmethyloxy]-phenyl | 4-F | H | | 467 |
| 42 | 3-[3-(RS)-hydroxypyrrolidin-1-ylcarbonylmethoxyloxy]-phenyl | 4-F | H | | 438 |
| 43 | 3-aminophenyl | 4-F | H | 165.2–165.8 | |
| 44 | 3-(imidazol-1-ylpropoxy)phenyl | 4-F | H | | 405 |
| 45 | 3-[3-(4-(RS)-hydroxypiperidin-1-yl)propoxy]phenyl | 4-F | H | | 438 |
| 46 | 3-(piperazin-1-yl)phenyl | 4-F.2HCl | H | 163.2–163.6 | |
| 47 | 3-(2-aminoethyl)phenyl | 4-F.HCl | H | 240.6–240.8 | |
| 48 | 3-[3-(morpholin-4-yl)propylamino]phenyl | 4-F | H | | 423 |
| 49 | 3-[2-(morpholin-4-yl)ethylamino]phenyl | 4-F | H | | 409 |
| 50 | 3-(2-aminosulfonylethyl)phenyl | 4-F | H | 170–170.4 | |
| 51 | 3-(piperidin-3-yl)phenyl | 4-F | H | 222.4–223 | |
| 52 | 3-(3-dimethylaminopropylamino)phenyl | 4-F | H | | 381 |
| 53 | 3-[2-(3-(RS)-hydroxypyrrolidin-1-yl)ethylamino]phenyl | 4-F | H | | 423 |
| 54 | 3-(2-hydroxyethoxy)phenyl | 4-F | H | | 341 |
| 55 | 3-[3-(morpholin-4-yl)prop-1-ynyl]phenyl | 2-F | 4-F | 190.4–191.2 | |
| 56 | 3-[3-(morpholin-4-yl)propyl]phenyl | 2-F | 4-F | 226.4–227.5 | |
| 57 | 3-(2-aminopyridin-5-yl)phenyl | 2-F.HCl | 4-F | 281.2–281.6 | |
| 58 | 3-(pyrimidin-3-yl)phenyl | 4-F | H | 237–241 | |
| 59 | 3-(1-methylpyridin-3-yl)phenyl.iodide | 4-F | H | 191.1–192.4 | |

-continued

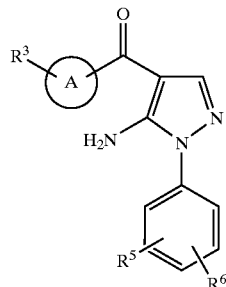

| CPD # | R³ ⟨A⟩ | R⁵ | R⁶ | M. Pt. ° C. | Mass Spec. (M⁺) |
|---|---|---|---|---|---|
| 60 | 3-(N-oxidopyridin-3-yl)phenyl | 2-F | 4-F | 251.1–251.7 | |
| 61 | 3-(pyridin-4-yl)phenyl | 2-F.HCl | 4-F | 218–226 | 376 |
| 62 | 3-(2-aminopyrimidin-5-yl)phenyl | 2-F.HCl | 4-F | 272–275 | |
| 63 | 3-(2-amino-6-methylpyridin-5-yl)phenyl | 2-F.HCl | 4-F | 215–217 | |
| 64 | 3-(6-methylpyridin-2-yl)phenyl | 2-F.HCl | 4-F | 268–279 | |
| 65 | 3-(pyridin-3-yl)phenyl | 4-Me.HCl | H | 281.3–282.8 | |
| 66 | 3-(pyridin-3-yl)phenyl | H.HCl | 3-MeO | 256.1–256.5 | |
| 67 | 3-(pyridin-3-yl)phenyl | 3-HO.HCl | H | 269–273 | |
| 68 | 3-(pyridin-3-yl)phenyl | 4-sulfamoyl | H.HCl | >300 | 419 |
| 69 | 3-(pyridin-3-yl)phenyl | 2-Me.HCl | 4-Me | 250.7–251.8 | |
| 70 | 3-(N-oxidopyridin-3-yl)phenyl | 2-Me | H | 190.5–191.2 | |
| 71 | 3-(N-oxidopyridin-3-yl)phenyl | 4-Me | H | 212–213.5 | |
| 72 | 3-(2,6-dimethylpyridin-3-yl)phenyl | 2-F.HCl | 4-F | >300 | 440.879 |
| 73 | 3-(pyridin-3-yl)phenyl | 2-Me.HCl | 4-Cl | | 425.317 |
| 74 | 3-(pyridin-3-yl)phenyl | 3-Me.HCl | 4-Me | | 404.899 |
| 75 | 3-(pyridin-3-yl)phenyl | 4-methylsulfonyl | H.HCl | | 454.936 |
| 76 | 3-(pyridin-3-yl)phenyl | 2-Et.HCl | H | | 404.899 |
| 77 | 3-(imidazol-2-yl)phenyl | 2-F.HCl | 4-F | | |
| 78 | 3-(3-ethoxycarbonylphenyl)phenyl | 4-F | H | 267.4–268.7 | |
| 79 | 3-(pyridin-3-yl)phenyl | 4-OH.HCl | H | | |
| 80 | 3-(3-carboxyphenyl)phenyl | 4-F | H | 117–128 | 429 |
| 81 | 3-[2-(piperidin-1-yl)ethoxy]phenyl | 4-F.HCl | H | 210.2–211.2 | |
| 82 | 3-(pyridin-2-ylmethoxy)phenyl | 4-F | H | 176.1–177.3 | |
| 83 | 3-isopropylaminocarbonyloxyphenyl | 4-F | H | 225.2–230.1 | |
| 84 | 3-ethylaminocarbonyloxyphenyl | 4-F | H | 201.2–202.8 | |
| 85 | 3-(1,2-dihydroxyethyl)phenyl | 4-F | H | 52–56 | 341.34 |
| 86 | 3-(1-piperidinylmethyl)phenyl | 2-F | 4-F | 116.6 . 118.6 | 396.439 |
| 87 | 3-(3-hydroxy-3-methyl-but-1-ynyl)phenyl | 4-F | H | 152.6–153.1 | |
| 88 | 3-(3-pyridylethynyl)phenyl | 2-F | 4-F | 183.5–184.0 | |
| 89 | 3-[3-(S,S-dioxo-thiomorpholin-4-yl)-1-propynyl]phenyl | 2-F | 4-F | 190.1–191.2 | |
| 90 | 3-(3-hydroxy-3-methylbutyl)phenyl | 4-F | H | 101.3–102.8 | |
| 91 | 3-(3-pyridylethyl)phenyl | 2-F | 4-F | 153.4–153.7 | |
| 92 | 3-[3-(S,S-dioxo-thiomorpholin-4-yl)propyl]phenyl | 2-F | 4-F | 123.8–125.9 | |
| 93 | 3-[2-(1-hydroxycyclopentyl)ethyl]phenyl | 4-F | H | 128.4–129.7 | |
| 94 | 3-[2-(1-hydroxycyclopentyl)ethynyl]phenyl | 2-F | 4-F | 176.8–177.1 | |
| 95 | 3-[2-(1-hydroxycyclopentyl)ethyl]phenyl | 2-F | 4-F | 120.3–121 | |
| 96 | 3-(3-hydroxybutyl)phenyl | 2-F | 4-F | 111.1–112.6 | |
| 97 | 3-[2-(morpholin-4-yl)ethoxy]phenyl | 2-F | H | 130.8–135.1 | |
| 98 | 3-[2-(morpholin-4-yl)ethoxy]phenyl | 2-Cl | 6-Cl | 144.2–145.1 | |
| 99 | 3-(pyridin-3-yl)phenyl | 2-F.HCl | 4-F | 256.5–257.7 | |
| 100 | 3-(2-methylsulfonylethyl)phenyl | 4-F | H | 151.5 . 155.6 | |
| 101 | 3-(2-methylsulfonylethyl)phenyl | 2-F | 4-F | 157.2–157.7 | |
| 102 | 3-(2-ethylsulfonylethenyl)phenyl | 2-F | 4-F | 101.6–105.6 | |
| 103 | 3-(1,2-dihydroxyethyl)phenyl | 2-F | 4-F | 59–64 | |
| 104 | 3-(2,2-dimethyl-1,3-dioxalan-5-yl)phenyl | 4-F | H | 94.5–100 | |
| 105 | 3-hydroxymethylphenyl | 2-F | 4-F | 155.4–156.5 | |
| 106 | 3-[2(R),3-dihydroxypropoxy]phenyl | 4-F | H | 150.2–153.0 | |
| 107 | 3-[2(S),3-dihydroxypropoxy]phenyl | 4-F | H | 149.9–153.0 | |
| 108 | 3-(2-hydroxyethylsulfonyl)phenyl | 2-F | 4-F | 92.1–93.8 | |
| 109 | 3-(1,2-dihydroxyethyl)phenyl | 2-Me | H | 83.0–85.5 | |
| 110 | 3-[2-(N-oxidomorpholin-4-yl)ethoxy]phenyl | 4-F | H | 185–186dec | |
| 111 | 3-[2-(morpholin-4-yl)ethoxy]phenyl | 2-F | 6-F | 178.9–181.2 | |
| 112 | 3-(2,3-dihydroxypropyl)phenyl | 2-F | 4-F | 140–142 | |
| 113 | 3-(2-hydroxyethyloxy)phenyl | 4-F | H | 165.3–166.7 | |
| 114 | 2-thienyl | 4-F | H | | 287 |
| 115 | 2-furyl | 4-F | H | | 271 |
| 116 | 2-methyl-3-furyl | 2-F | 4-F | | |
| 117 | 6-quinolinyl | 2-F | 4-F | 220–259.2 | |

-continued

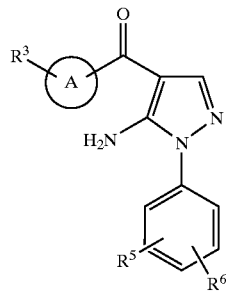

| CPD # | R³ ⓐ | R⁵ | R⁶ | M. Pt. ° C. | Mass Spec. (M⁺) |
|---|---|---|---|---|---|
| 118 | 2-hydroxyethylphenyl | 4-F | H | 154.5–155.0 | |
| 119 | 3-carboxymethyloxyphenyl | 4-F | H | 215.9–216.2 | |
| 120 | 3-(pyridin-3-yl)phenyl | 2-Me | H | 223.7–225.1 | |
| 146 | 3-(3-sulfamoylphenyl)phenyl | 4-F | H | 214.6–217.5 | |
| 147 | 3-(3-methylsuflonylphenyl)phenyl | 4-F | H | | |
| 148 | 3-methylsulfonylmethylphenyl | 4-F | H | | 373 |
| 149 | 3-sulfamoylmethylphenyl | 4-F | H | | |
| 150 | 3-carboxymethylphenyl | 4-F | H | | |
| 151 | 3-(2-hydroxyethylsulfonyl)phenyl | 4-F | H | | |
| 152 | 3-[(2,2-dimethyl-1,3-dioxalan-5-yl)methoxy]phenyl | 4-F | H | | |
| 153 | 3-oxiranylmethoxyphenyl | 4-F | H | | |
| 154 | 3-[2(R),3-dihydroxypropoxy]phenyl | 2-F | 4-F | 115.6–116.9 | |
| 155 | 3-[2(R),3-dihydroxypropoxy]phenyl | 2-Me | H | | 368 (M + H) |
| 156 | 3-[2(R),3-dihydroxy-3,3-dimethylpropoxy]phenyl | 4-methylsulfonyl | H | | 433 |
| 157 | 3-[2(R),3(R)-dihydroxy-3-methylpropoxy]phenyl | 4-F | H | | |
| 158 | 3-[2(R),3(S)-dihydroxy-3-methylpropoxy]phenyl | 4-F | H | | |
| 159 | 3-[2(S),3(S)-dihydroxy-3-methylpropoxy]phenyl | 4-F | H | | |
| 160 | 3-[2(S),3(R)-dihydroxy-3-methylpropoxy]phenyl | 4-F | H | | |
| 161 | 3-[2(R),3-dihydroxy-3,3-dimethylpropoxy]phenyl | 4-F | H | | |
| 162 | 3-[2(S),3-dihydroxy-3,3-dimethylpropoxy]phenyl | 4-F | H | | |
| 163 | 3-[3,4-dihydroxycyclopentyloxy]phenyl | 4-F | H | | |
| 164 | 3-[2-(1,3-dihydroxy)propoxy]phenyl | 4-F | H | | |

Compounds 121–145 are listed in the Tables following Example 14,15,19 and 23.

PREFERRED EMBODIMENTS

While the broadest definition of this invention is set forth in the Summary of the Invention, certain compounds of Formula (I) are preferred. For example, (I) A preferred group of compounds is that wherein $R^3$ is selected from:
(a) optionally substituted heterocyclyl;
(b) aryl or heteroaryl both optionally substituted with a substituent selected from halo, alkyl, amino, alkoxy, carboxy, lower alkoxy carbonyl, SO₂R' (where R' is alkyl) or SO₂NHR'R" (where R' and R" are independently hydrogen or alkyl);
(c) heteroalkyl;
(d) heteroalkenyl;
(e) heteroalkylamino;
(f) heteroalkoxy;
(g) optionally substituted heterocyclylalkyl or heterocylyloxy;
(h) optionally substituted heterocyclylalkenyl;
(i) optionally substituted heterocyclylalkynyl;
(j) optionally substituted heterocyclylalkoxy;
(k) optionally substituted heterocyclylalkylamino;
(l) optionally substituted heterocyclylalkylcarbonyl;
(k) —Y-(alkylene)-$R^9$ where Y is a single bond, —O— or —NH— and $R^9$ is optionally substituted heteroaryl, —CONR$^{12}$R$^{13}$, SO₂R$^{14}$, —SO₂NR$^{15}$R$^{16}$ —NHSO₂R$^{17}$ or —NHSO₂NR$^{18}$R$^{19}$ where R$^{12}$, R$^{13}$, R$^{14}$, R$^{15}$, R$^{16}$ R$^{17}$, R$^{18}$ and R$^{19}$ are independently of each other hydrogen, alkyl or heteroalkyl;
(l) cycloalkylalkyl, cycloalkylalkynyl and cycloalkylalkynyl, all optionally substituted with alkyl, halo, hydroxy or amino;
(m) arylaminoalklene or heteroarylaminoalkylene; or
(n) Z-alkylene-NR$^{30}$R$^{31}$ where Z is —NH—, —N(alkyl)— or —O—, and R$^{30}$ and R$^{31}$ are independently of each other, hydrogen, alkyl or heteroalkyl. Within the above preferred group, more preferred groups of compounds are those wherein, A and B are aryl, preferably phenyl.

Within the above preferred and more preferred groups, an even more preferred group of compounds is that wherein:

$R^1$ is hydrogen;
$R^2$ is hydrogen or alkyl, preferably hydrogen or methyl, more preferably hydrogen.
$R^4$ is hydrogen, halo or alkyl, preferably hydrogen, chloro, fluoro or methyl, more preferably hydrogen.

Within the above preferred and more preferred groups, a particularly preferred group of compounds is that wherein $R^3$ is at the 3-position and is optionally substituted heteroaryl, preferably pyridinyl, N-oxidopyridinyl or pyridonyl.

Another particularly preferred group of compounds is that wherein $R^3$ is at the 3-position and is optionally substituted phenyl, preferably sulfamoylphenyl, alkylsulfamoylphenyl, carboxyphenyl, carboxamidophenyl, alkoxycarbonylphenyl, alkylaminocarbonylphenyl or dialkylaminocarbonylphenyl.

A third particularly preferred group of compounds is that wherein:

$R^3$ is at the 3-position and is selected from:
(a) heteroalkyl;
(b) heteroalkoxy;
(c) heteroalkylamino;
(d) optionally substituted heterocyclalkyl;
(e) optionally substituted heterocyclylalkoxy;
(f) optionally substituted heterocyclylalkylamino;
(g) —Y-(alkylene)-$R^9$ where Y is a single bond, —O— or —NH— and $R^9$ is optionally substituted heteroaryl, —$CONR^{12}R^{13}$, $SO_2R^{14}$, —$SO_2NR^{15}R^{16}$—$NHSO_2R^{17}$ or —$NHSO_2NR^{18}R^{19}$ where $R^{12}$, $R^{13}$, $R^{14}$, $R^{15}$, $R^{16}$ $R^{17}$, $R^{18}$ and $R^{19}$ are independently of each other hydrogen, alkyl or heteroalkyl; or
(h) Z-alkylene-$NR^{30}R^{31}$ where Z is —NH—, —N(alkyl)— or —O—, and $R^{30}$ and $R^{31}$ are independently of each other, hydrogen, alkyl or heteroalkyl.

Preferred groups for $R^3$ include amino, 3-dimethylaminopropoxy, 2-dimethylaminoethoxy, 2-dimethylaminoethyl, 3-dimethylaminopropyl, 4-dimethylaminobutyl, 2-dimethylaminoethylamino, 3-dimethylaminopropylamino, 3-dimethylaminoprop-1-enyl, 3-dimethylaminoprop-1-ynyl and 2-dimethylaminoethylcarbonyl, preferably amino.

Another group of preferred groups for $R^3$ is selected from 3-(morpholin-4-yl)propoxy, 2-(morpholin-4-yl)ethoxy, 3-(morpholin-4-yl)propyl, 2-(morpholin-4-yl)ethyl, 4-(morpholin-4-yl)butyl, 3-(morpholin-4-yl)propylamino, 2-(morpholin-4-yl)-ethylamino, 3-(morpholin-4-yl)-prop-1-enyl, 3-(morpholin-4-yl)prop-1-ynyl, 4-methylpiperazin-1-yl, piperazin-1-yl, pyridin-3-yl, morpholin-4-ylmethylcarbonyl, 3-dimethylaminoprop-1-enyl, 3-dimethylaminoprop-1-ynyl, 2-aminosulfonylethyl, 2-aminosulfonylethenyl, acetylamino and trifluoroacetylamino, preferably 2-(morpholin-4-yl)ethoxy and 3-(morpholin-4-yl)-propyl.

A fourth group of particularly preferred compounds is that where $R^5$ is halo or alkyl and $R^6$ is hydrogen, halo or alkyl, preferably $R^5$ is 4-F or 2-Me and $R^6$ is hydrogen, or $R^5$ is 2-F and $R^6$ is 4-F.

Exemplary Particularly Preferred Compounds are:

5-amino-1-(4-fluorophenyl)-4-[3-(2-morpholin-4-ylethoxy)benzoyl]pyrazole.
5-amino-1-(2,4-difluorophenyl)-4-[3-(3-morpholin-4-ylpropyl)benzoyl]pyrazole.
5-amino-4-(3-aminobenzoyl)-1-(4-fluorophenyl)pyrazole.
5-amino-1-(4-fluorophenyl)-4-[3-(3-morpholin-4-ylpropyl)benzoyl]pyrazole.
5-amino-4-[3-(2-aminosulfonylethenyl)benzoyl]-1-(4-fluorophenyl)pyrazole.
5-amino-4-(3-acetylaminobenzoyl)-1-phenylpyrazole.
5-amino-4-[3-(2-aminoethyl)benzoyl]-1-(4-fluorophenyl)pyrazole.
5-amino-1-(4-fluorophenyl)-4-[3-(3-morpholin-4-ylpropylamino)benzoyl]pyrazole.
5-amino-4-[3-(2-aminosulfonylethyl)benzoyl]-1-(4-fluorophenyl)pyrazole.
5-amino-1-(4-fluorophenyl)-4-[3-(pyridin-3-yl)benzoyl]pyrazole.
5-amino-1-(2-methylphenyl)-4-[3-(pyridin-3-yl)benzoyl]pyrazole.
5-amino-1-(2-methylphenyl)-4-[3-(N-oxidopyridin-3-yl)benozyl]pyrazole.
5-amino-4-[3-(2,3-dihydroxypropoxy)benzoyl]-1-(4-fluorophenyl)pyrazole.
5-amino-4-[3-(1,2-dihydroxyethyl)benzoyl]-1-(4-fluorophenyl)pyrazole.
5-amino-1-(4-fluorophenyl)-4-[3-sulfamoylbenzoyl]pyrazole.

GENERAL SYNTHETIC SCHEME

Compounds of this invention can be made by the methods depicted in the reaction schemes shown below.

The starting materials and reagents used in preparing these compounds are their available from commercial suppliers such as Aldrich Chemical Co., (Milwaukee, Wis., USA), Bachem (Torrance, Calif., USA), Emka-Chemie, or Sigma (St. Louis, Miss., USA) or are prepared by methods known to those skilled in the art following procedures set forth in references such as *Fieser and Fieser's Reagents for Organic Synthesis,* Volumes 1–17 (John Wiley and Sons, 1991); *Rodd's Chemistry of Carbon Compounds,* Volumes 1–15 and Supplementals (Elsevier Science Publishers, 1989), *Organic Reactions,* Volumes 1–40 (John Wiley and Sons, 1991), *March's* Advanced Organic Chemistry, (John Wiley and Sons, 4th Edition), and *Larock's* Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

PREPARATION OF COMPOUNDS OF FORMULA (I)

Schemes A, B and C describe methods to generate the compounds of Formula (I).

Scheme A

Compounds of Formula (I) where $R^2$ is hydrogen and other groups are as defined in the Summary of the Invention are prepared as described below.

Scheme A
Compounds of Formula (I) where $R^2$ is hydrogen and other groups are as defined in the Summary of the invention are prepared as described below.

Method (a)

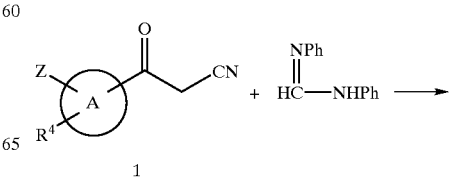

1

-continued

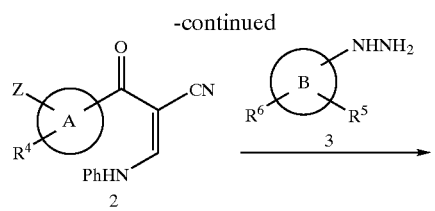

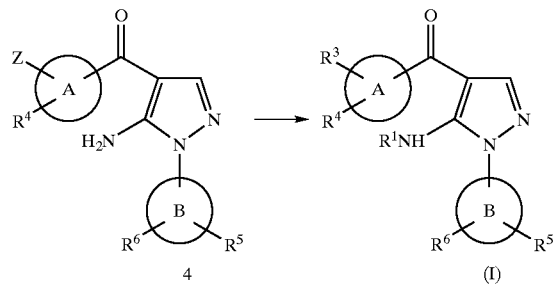

Method (b)

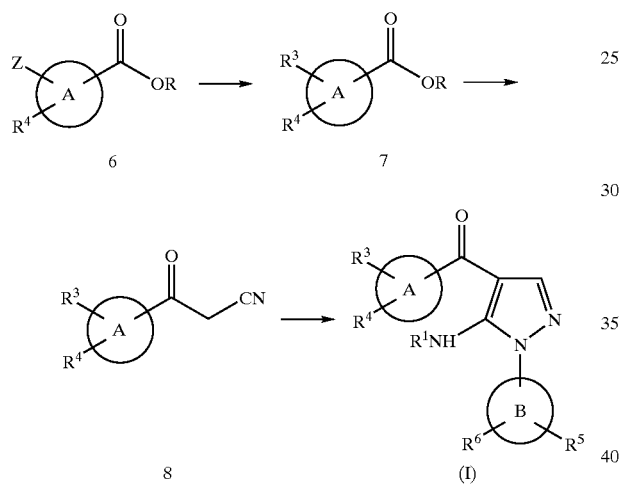

4-fluorophenylhydrazine, phenylhydrazine, 2-hydrazinopyridine, 2-hydrazinobenzothiazole, 2-hydrazinoquinoline etc., are commercially available.

Compound 4 is then converted to a compound of Formula (I) where $R^1$ is hydrogen and $R^3$ is as defined in the Summary of the Invention by methods well known in the art. Some such procedures are described below.

(i) A compound of Formula (I) where $R^3$ is heterocyclylalkyloxy can be prepared from a compound of formula 4 where Z is alkoxy as shown below:

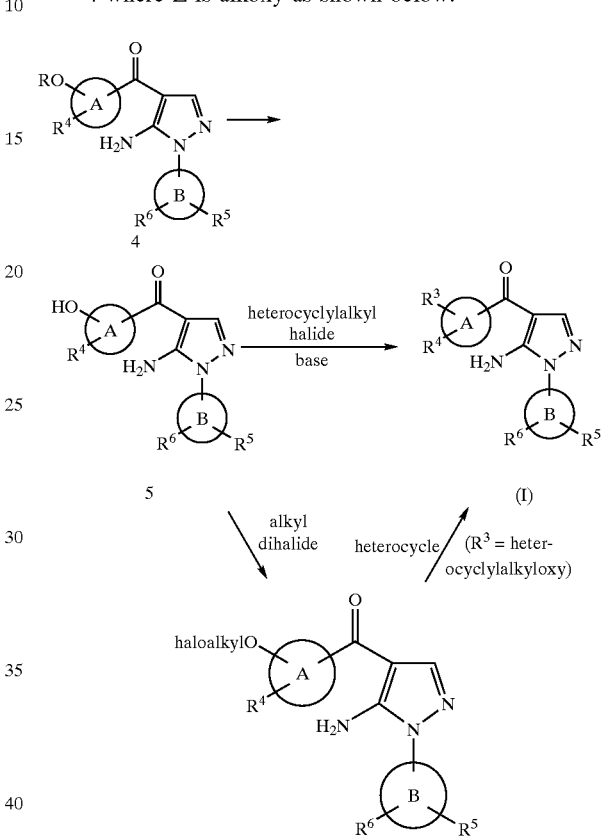

In general, compounds of Formula (I) can be prepared by following either method (a) or (b) as described below.

Method (a)

Reaction of a 2-ketoacetonitrile of formula 1 [where Z is halo (e.g., bromo or iodo), alkoxy, nitro or acetylamino] with N,N-diphenylformamidine gives a 2-keto-3-phenylaminoacrylonitrile of formula 2. The reaction occurs upon heating in a high boiling aromatic hydrocarbon such as toluene, xylene, and the like.

In general, compounds of formula 1 are either commercially available or they can be prepared by methods well known in the art. For example, 2-aroylacetonitriles of formula 1 such as 4-methoxybenzoylacetonitrile, 3-nitrobenzoylacetonitrile are commercially available. Others can be prepared by treating acetonitrile with a base such as n-butyllithium followed by reaction of the formed acetonitrile anion with an aroyl/heteroaroyl halide or an aryl/heteroaryl ester as described in Sjogren, E. B., et al., *J. Med. Chem.*, 34, 3295, (1991).

Reaction of the 2-keto-3-phenylaminoacrylonitrile of formula 2 with a hydrazine of formula 3 provides a 5-amino-4-ketopyrazole of formula 4. This reaction is generally carried out in a polar solvent such as ethanol, isopropanol, and the like. Aryl/heteroaryl hydrazines of formula 3 such as 2- or 3-chlorophenylhydrazine, 2-, 3-, or A compound of Formula (I) where $R^3$ is heterocyclylalkyloxy can be prepared from a compound of formula 4 where Z is alkoxy be first de-alkylating the alkoxy group to give the corresponding compound of formula 5 where Z is hydroxy followed by reaction with a heterocyclylalkyl halide [e.g., 4-(2-chloroethyl)morpholine, 1-(2-chloroethyl) pyrrolidine, and the like]. The de-alkylation reaction is carried out either with boron tribromide in a halogenated organic solvent such as dichloromethane or by heating 4 in neat pyridinium hydrochloride. The alkylation is carried out in the presence of a base (such as potassium carbonate, cesium carbonate, and the like) in a polar organic solvent such as acetonitrile, dimethylformamide, acetone, and the like.

Alternatively, a heterocyclylalkyl group can be attached by reacting 5 with an alkyl dihalide followed by the reaction of the resulting haloalkyloxy intermediate with a heterocyclyl group (e.g., piperazine, morpholine, pyrrolidine, and the like) under the reaction conditions described above. Alkyl dihalides such as 1-bromo-2-chloroethane, 1-chloro-3-iodopropane, and the like, are commercially available.

(ii) A compound of Formula (I) where $R^3$ is —O—(alkylene)-$R^9$ (where $R^9$ is —COOH, —COR$^{10}$, —COOR$^{11}$ or —CONR$^{12}$R$^{13}$) can be prepared from a compound of formula 5 as shown below:

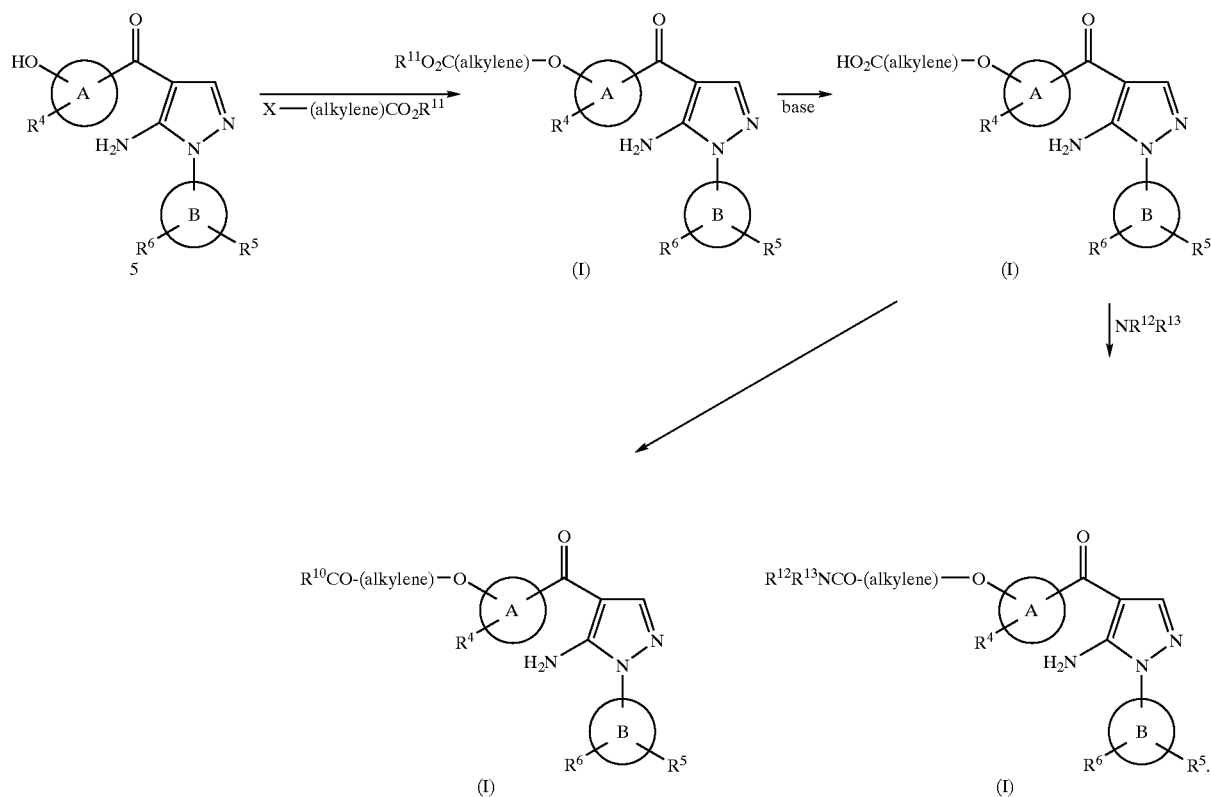

A compound of Formula (I) where $R^3$ is —O—(alkylene)—COOR$^{11}$ is prepared by reacting a compound of formula 5 with an alkylating agent of formula X-(alkylene)-CO$_2$R$^{11}$ where X is a halo group. Hydrolysis of the ester group provides the free acid ($R^9$ is —COOH) which can be converted to a compound of Formula (I) where $R^9$=—CONR$^{12}$R$^{13}$, is desired, by treating the acid with an amine of formula NR$^{12}$R$^{13}$ (where $R^{12}$ and $R^{13}$ are as defined in the Summary of the Invention) in the presence of a suitable coupling agent (e.g., carbonyl diimidazole, N,N-dicyclohexylcarbodiimide and the like).

A compound of Formula (I) where $R^9$ is —COR$^{10}$ can be prepared from a compound of Formula (I) where $R^9$ is —COOH by first converting the acid to a Weinreb amide followed by treatment with either a Grignard reagent or organolithium reagent of formula R$^{10}$MgBr or R$^{10}$Li, respectively.

(iii) A compound of Formula (I) where $R^3$ is —NH-(alkylene-$R^9$ where $R^9$ is —COOH, —COR$^{10}$, —COOR$^{11}$, —CONR$^{12}$R$^{13}$ or heterocyclylalkylamino can be prepared from a compound of formula 4 where Z is a nitro group by reducing the nitro group to the amino group and then following the procedures described above.

(iv) A compound of Formula (I) where $R^3$ is heteroalkenyl, heteroalkynyl, heterocyclylalkenyl, heterocyclylalkynyl, heteroalkyl or heterocyclylalkyl can be prepared as shown below.

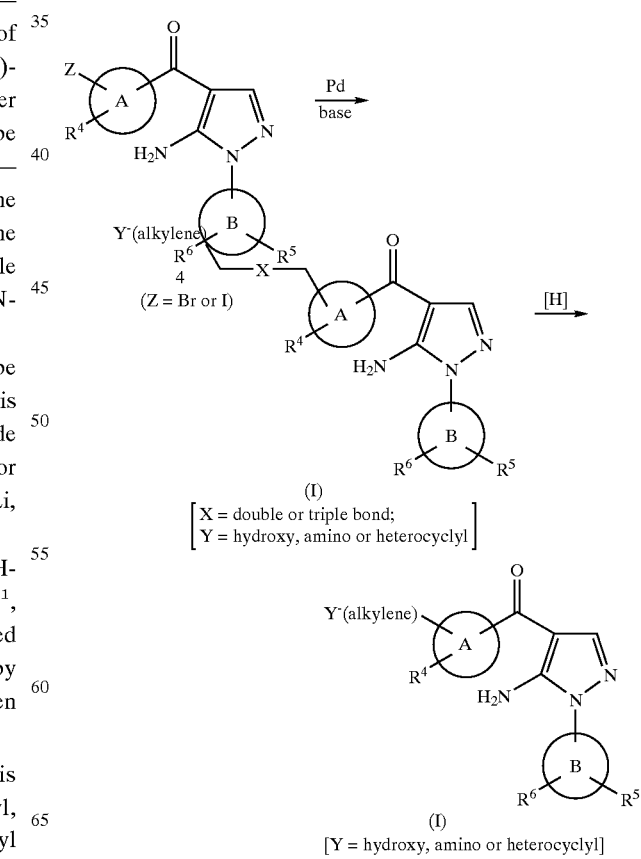

A compound of Formula (I) where $R^3$ is heteroalkenyl, heteroalkynyl, heterocyclylalkenyl or heterocyclylalkynyl can be prepared by reacting a compound of formula 4 where Z is halo with a heteroalkene, heteroalkyne, heterocyclylalkene or heterocyclylalkyne respectively in the presence of a palladium (II) catalyst such as dichlorobis (triphenylphosphine)-palladium (II) in an organic base such as diisopropylamine, and the like. Heteroalkenes, heteroalkynes such as allyl alcohol, propargyl alcohol, 3-butyn-1-ol, propargylamine are commercially available. Heterocyclylalkyne can be prepared by reacting an alkynyl halide with a heterocycle. For example, 3-morpholin-1-ylprop-1-yne can be prepared by reacting propargyl bromide with morpholine. Reduction of the double or triple bond under catalytic hydrogenation reaction conditions provides the corresponding compound of Formula (I) where $R^3$ is a heterocyclylalkyl or heteroalkyl group.

(v) A compound of Formula (I) where $R^3$ is —$NHSO_2R^6$, —$NHSO_2NR^7R^8$ or $NHC(X)R^{23}R^{24}$ (where X is —O— or —S—) can be prepared from a compound of Formula (I) where $R^3$ is amino by following the synthetic procedures described in PCT Application No. WO 97/46524.

A compound of Formula (I) where $R^1$ is an acyl group can be prepared by reacting the the corresponding compound of Formula (I) where $R^1$ is hydrogen with an acylating reagent of formula $R^1COL$ where L is a leaving group under acylating reaction conditions such as halo. The reaction is carried out in the presence of a base such as sodium hydroxide, cesium carbonate, and the like.

Method (b)

Alternatively, a compound of Formula (I) can be prepared from an ester of formula 6 where Z is as defined above, by first converting the Z group in compound 6 to the desired $R^3$ group utilizing the reaction conditions described in method (a)(i–v) above. Condensation of 7 with acetonitrile anion gives a 2-ketoacetonitrile of formula 8 which is then converted to a compound of Formula (I) utilizing the reaction conditions described in method (a) above.

Compounds of Formula (I) where $R^2$ is thioalkyl or alkyl can be prepared by following the procedures described in U.S. Pat. No. 5,712,303.

Scheme B

An alternate synthesis of compounds of Formula (I) where $R^2$ is hydrogen and other groups are as defined in the Summary of the Invention is described below.

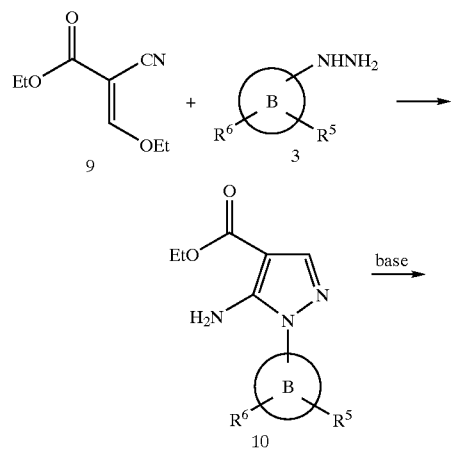

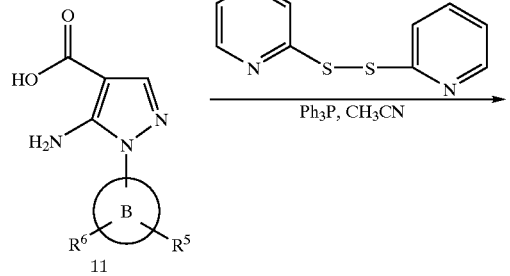

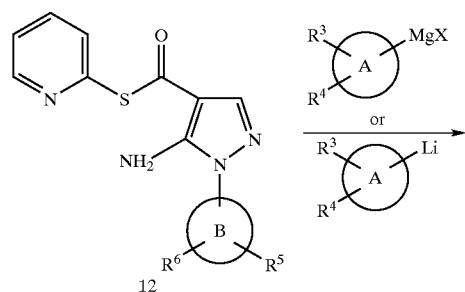

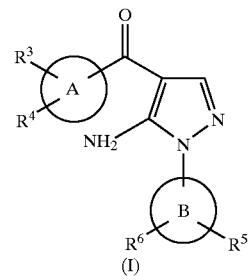

Condensation of 2-cyano-3-ethoxyacrylate of formula 9 with a hydrazine of formula 3 provides a 5-amino-4-ethoxycarbonyl pyrazole of formula 10. The condensation reaction is carried out in a suitable polar organic solvent such as ethanol, isopropanol, and the like. Hydrolysis of 10 with an aqueous base (e.g., sodium hydroxide, lithium hydroxide, and the like) in an alcoholic organic solvent (e.g., methanol, ethanol, and the like) provides the corresponding 5-amino-4-carboxypyrazole of formula 11. Treatment of 11 with dipyridyldisulfide followed by reaction of the resulting thiopyridyl ester derivative 12 with an organometallic reagent such as a Grignard reagent or an organolithium reagent shown above provides a compound of Formula (I).

Scheme C

Another alternate synthesis of compounds of Formula (I) where $R^2$ is hydrogen and other groups are as defined in the Summary of the Invention is described below.

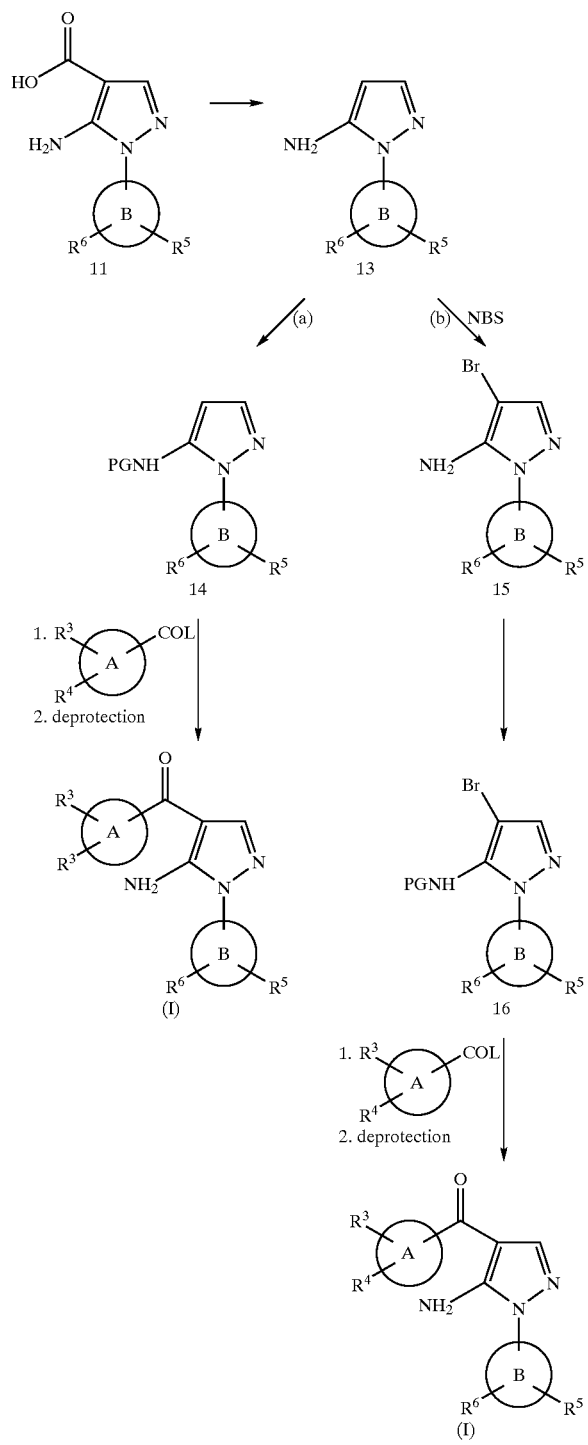

Thermal decarboxylation of a 5-amino-4-carboxypyrazole of formula 11 gives the corresponding 5-aminopyrazole of formula 13. Compound 13 is then converted to a compound of Formula (I) as shown in method (a) or (b) above.

In method (a), a compound of formula 13 is converted to a compound of Formula (I) by first protecting the amino group in compound 13 with a suitable amino protecting group (e.g., tert-butoxycarbonyl, and the like) to give the corresponding amino-protected compound of formula 14. Treatment of 14 with an acid derivative of formula $R^3COL$ where L is a leaving group under organometallic displacement reaction conditions [e.g., alkoxy (preferably methoxy or ethoxy), dialkylamino, preferably N,O-dimethylhydroxylamino] followed by the removal of the amino protecting group then provides a compound of Formula (I). The nucleophilic substitution is carried out in the presence of 2 equivalents of an alkyllithium (e.g., tert-butyllithium, and the like) and in an aprotic organic solvent such as tetrahydrofuran. The reaction conditions employed for the removal of the amino protecting group depends on the nature of the protecting group. For example, if tert-butoxycarbonyl is the protecting group, it is removed by treatment with an acid such as trifluoroacetic acid, hydrochloric acid, and the like.

Acid derivatives of formula $R^3COL$ can be prepared by methods well known in the field of organic chemistry. For example, an acid derivative where L is a N,O-dimethylhydroxylamino group can be prepared from its corresponding acid by first converting the acid to the acid chloride with a suitable chlorinating agent such as oxalyl chloride, followed by treatment with N,O-dimethylhydroxylamine hydrochloride in the presence of an organic base such as triethylamine.

In method (b), a compound of formula 10 is brominated to give the 5-amino-4-bromopyrazole of formula 15. The bromination reaction is carried out with a suitable brominating agent such as N-bromosuccinimide in a suitable polar organic solvent such as dimethylformamide. Compound 15 is then converted to a compound of Formula (I) utilizing the reaction conditions described in Scheme C, method (a) above.

UTILITY, TESTING, AND ADMINISTRATION

Utility

The compounds of Formula (I) are p38 MAP kinase inhibitors and therefore compounds of Formula (I) and compositions containing them are useful in the treatment of diseases such as rheumatoid arthritis, osteoarthritis, spondylitis, bone resorption diseases, sepsis, septic shock, toxic shock syndrome, endotoxic shock, tuberculosis, atherosclerosis, diabetes, adult respiratory distress syndrome, chronic pulmonary inflammatory disease, fever, periodontal diseases, ulcerative colitis, pyresis, Alzheimer's and Parkinson's diseases.

Testing

The ability of the compounds of Formula (I) to inhibit p38 MAP kinase was demonstrated by the in vitro assay described in Example 15. The ability of the compounds of Formula (I) to inhibit the release of TNF-α was demonstrated by the in vitro and the in vivo assays described in detail in Examples 16 and 17, respectively. The anti-inflammatory activity of the compounds of this invention was determined utilizing adjuvant induced arthritis in rats assay described in Example 18.

Administration and Pharmaceutical Compositions

In general, the compounds of this invention will be administered in a therapeutically effective amount by any of the accepted modes of administration for agents that serve similar utilizes. The actual amount of the compound of this invention, i.e., the active ingredient, will depend upon numerous factors such as the severity of the diseases to be treated, the age and relative health of the subject, the potency of the compound used, the route and form of administration, and other factors.

Therapeutically effective amounts of Formula (I) may range from approximately 0.1–50 mg per kilogram body weight of the recipient per day; preferably about 1–30 mg/kg/day. Thus, for administration to a 60 kg person, the dosage range would most preferably to about 70 mg to 2.1 g per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula (I) in combination with at least one pharmaceutically acceptable excipient. Acceptable excipients are non-toxic, aid administration, and do not adversely affect the therapeutic benefit of the compound of Formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in *Remington's Pharmaceutical Sciences*, edited by E. W. Martin (Mack Publishing Company, 18th ed. 1990).

The amount of the compound in a formulation can vary within the full range employed by those skilled in the art. Typically, the formulation will contain, on a weight percent (wt %) basis, from about 0.01–99.99 wt % of a compound of Formula (I) based on the total formulation, with the balance being one or more suitable pharmaceutical excipients. Preferably, the compound is present at a level of about 1–80 wt %. Representative pharmaceutical formulations containing a compound of Formula (I) are described in Example 14.

EXAMPLES

The following preparations and examples are given to enable those skilled in the art to more clearly understand and to practice the present invention. They should not be considered as limiting the scope of the invention, but merely as being illustrative and representative thereof. Numbers in brackets refer to the CPD # in Table I.

Example 1

5-Amino-1-(4-fluorophenyl)-4-[3-[3-(morpholin-4-yl)prop-1-ynyl]benzoyl]pyrazole (3)

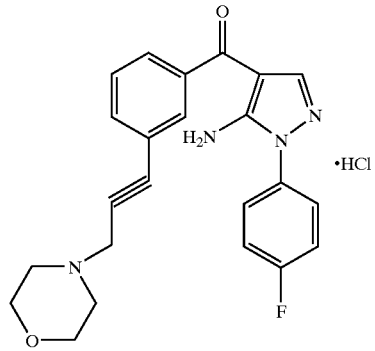

Step 1 n-Butyllithium (214 ml, 340 mmol, 1.6 M solution in hexane) was added dropwise to a solution of acetonitrile (23.8 ml, 460 mmol) in dry tetrahydrofuran (1000 ml) at −78° C. After stirring the reaction mixture for 20 min., a solution of 4-bromobenzoyl chloride in dry tetrahydrofuran (50 ml) was added dropwise over 20 min. After 1 h, saturated ammonium chloride was added (200 ml) and the reaction mixture was allowed to warm to room temperature. The product was extracted into ether and washed with 1N hydrochloric acid (400 ml). The organics were removed in vacuo and the residue was redissolved in ethyl acetate. Ammonium hydroxide was added to give a solid which was filtered, redissolved in ethyl acetate and washed with 2 N hydrochloric acid. The organic layer was washed with brine, dried over sodium sulfate and concentrated in vacuo to give 2-(3-bromobenzoyl)acetonitrile (16.6 g) as a solid.

Step 2

A mixture of 2-(3-bromobenzoyl)acetonitrile (16.5 g, 73.6 mmol) and N,N-diphenylformamidine (14.5 g, 73.6 mmol) in xylene (100 ml) was heated at reflux under a nitrogen atmosphere. After 3 h, the reaction was cooled to room temperature and diluted with ether to give 2-(3-bromobenzoyl)-3-phenylaminoacrylonitrile (17.9 g) as a solid.

Step 3

A mixture of 4-fluorophenylhydrazine (4.25 g, 33.7 mmol) and 2-(3-bromobenzoyl)-3-phenylaminoacrylonitrile (10.0 g, 30.7 mmol) in ethanol (100 ml) was heated at reflux under a nitrogen atmosphere. After 4 h, the reaction mixture was cooled to room temperature, diluted with hexane to give 5-amino-4-(3-bromobenzoyl)-1-(4-fluorophenyl)pyrazole (9.7 g) as a solid.

Replacing 4-fluorophenylhydrazine with 2,4-difluorophenylhydrazine in step 3 above gave 5-amino-4-(3-bromobenzoyl)-1-(2,4-difluorophenyl)pyrazole.

Step 4

A mixture of 5-amino-4-(3-bromobenzoyl)-1-(4-fluorophenyl)pyrazole (1.3 g, 4.16 mmol), 4-(prop-2-ynyl)morpholine (2.1 g, 16.6 mmol) [prepared by adding to a solution of morpholine (14.7 ml, 168 mmol) in ether (50 ml), propargyl bromide (7.5 ml, 84 mmol) in ether (50 ml) dropwise over 30 min. and heating the reaction mixture to reflux. After 16 h, the reaction mixture was cooled to room temperature and filtered through a Buchner funnel. The filtrate was concentrated and purified by flash chromatography (gradient elution, 20–100% EtOAc/hexane) to give 4-(prop-2-ynyl)morpholine (5.0 g)], bis(triphenylphosphine)-palladium chloride (0.29 g, 0.42 mmol) and copper iodide (0.079 g, 0.42 mmol) in diisopropylamine (60 ml) was heated at 70° C. under argon. After 10 h, the reaction mixture was cooled to room temperature, diluted with ethyl acetate, washed with brine and dried over sodium sulfate. The organics were removed in vacuo. The crude product was purified by flash chromatography (elution gradient, EtOAc-5% MeOH/EtOAc with 0.2% NH$_4$OH) to give 5-amino-1-(4-fluorophenyl)-4-[3-(3-morpholin-4-ylprop-1-ynyl)benzoyl]-pyrazole which was converted to the hydrochloride salt and recrystallized from a mixture of methanol/ethyl acetate/hexane to give (1.4 g) of the pure product.

Proceeding as described in Example 1 above but substituting 4-(prop-2-ynyl)-morpholine in Step 4 with:

1-(prop-2-ynyl)-4-methylpiperazine,
1-(prop-2-ynyl)piperidine,
2-propyn-1-ol,
1-dimethylamino-2-propyne, and
2-methyl-3-butyn-2-ol; gave
5-amino-1-(4-fluorophenyl)-4-{3-[3-(4-methylpiperazin-1-yl)prop-1-ynyl]benzoyl}pyrazole.2HCl (8),
5-amino-1-(4-fluorophenyl)-4-[3-{3-(piperidin-1-yl)prop-1-ylnyl}benzoyl]pyrazole.HCl (9),
5-amino-1-(4-fluorophenyl)-4-[3-(3-hydroxyprop-1-ynyl)benzoyl]pyrazole (7),
5-amino-4-[3-(3-dimethylaminoprop-1-ynyl)benzoyl]-1-(4-fluorophenyl)pyrazole.HCl (12), and
5-amino-1-(4-fluorophenyl)-4-[3-(3-hydroxy-3-methyl-but-1-ynyl)benzoyl]pyrazole (87), respectively.

Proceeding as described in Example 1 above but substituting 4-fluorophenylhydrazine in Step 3 with 2,4-difluorophenylhydrazine, and 4-(prop-2-ynyl)morpholine in Step 4 with 3-ethynylpyridine gave
5-amino-1-(2,4-difluorophenyl)-4-[3-(3-pyridylethynyl)benzoyl]pyrazole (88), with 3-(S,S-dioxo-thiomorpholin-4-yl)-1-propyne gave
5-amino-1-(2,4-difluorophenyl)-4-[3-{3-(S,S-dioxo-thiomorpholin-4-yl)-1-pyropynyl}benzoyl]pyrazole (89), and
with 1-ethynylcyclopentanol gave
5-amino-1-(2,4-difluorophenyl)-4-[3-(2-(1-hydroxycyclopentyl)ethynyl)benzoyl]pyrazole (94).

Example 2

5-Amino-1-(4-fluorophenyl)-4-[3-(3-morpholin-4-ylpropyl)benzoyl]-pyrazole hydrochloride (6)

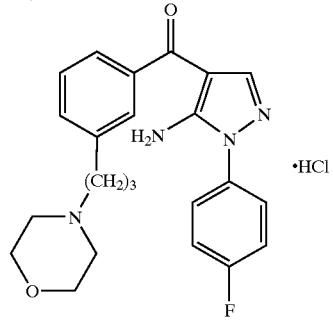

A mixture of 5-amino-1-(4-fluorophenyl)-4-[3-(3-morpholin-4-ylprop-1-ynyl)benzoyl]pyrazole (0.45 g, 1.0 mmol) [prepared as described in Example 1] and 5% Pd/C (0.07 g) in ethanol (20 ml) was stirred under hydrogen atmosphere. After 16 h, the reaction mixture was filtered through Celite® and the filtrate was concentrated in vacuo. The crude product was purified by flash chromatography (elution gradient, EtOAc-15% MeOH/EtOAc with 0.2% NH$_4$OH). The product was converted to the hydrochloride salt and recrystallized from a mixture of methanol/ethyl acetate to give 5-amino-1-(4-fluorophenyl)-4-[3-(3-morpholin-4-ylpropyl)benzoyl]pyrazole.HCl (0.3 g, mpt. 211.9–212.6° C.) as a solid.

Proceeding as described in Example 2 above, but substituting of 5-amino-1-(4-fluorophenyl)-4-[3-(3-morpholin-4-ylprop-1-ynyl)benzoyl]pyrazole with:
5-amino-1-(4-fluorophenyl)-4-{3-[3-(4-methylpiperazin-1-yl)prop-1-ynyl]benzoyl}pyrazole,
5-amino-1-(4-fluorophenyl)-4-[3-{3-(piperidin-1-yl)prop-1-ynyl}benzoyl]pyrazole,
5-amino-1-(4-fluorophenyl)-4-[3-(3-hydroxyprop-1-ynyl)benzoyl]pyrazole,
5-amino-4-[3-(3-dimethylaminoprop-1-ynyl)benzoyl]-1-(4-fluorophenyl)pyrazole,
5-amino-1-(4-fluorophenyl)-4-[3-(3-hydroxy-3-methyl-1-butynyl)benzoyl]pyrazole,
5-amino-1-(2,4-difluorophenyl)-4-[3-(3-pyridylethynyl)benzoyl]pyrazole,
5-amino-1-(2,4-difluorophenyl)-4-[3-{3-(S,S-dioxo-thiomorpholin-4-yl)-1-propynyl}benzoyl]pyrazole,
5-amino-1-(4-fluorophenyl)-4-[3-{2-(1-hydroxycyclopentyl)ethynyl)benzoyl]pyrazole, and
5-amino-1-(2,4-difluorophenyl)-4-[3-{2-(1-hydroxycyclopentyl)ethynyl}benzoyl]pyrazole gave
5-amino-1-(4-fluorophenyl)-4-{3-[3-(4-methylpiperazin-1-yl)propyl]benzoyl}pyrazole (30);
5-amino-1-(4-fluorophenyl)-4-[3-(3-piperidin-1-ylpropyl)benzoyl]pyrazole (32);
5-amino-1-(4-fluorophenyl)-4-[3-(3-hydroxypropyl)benzoyl]pyrazole;
5-amino-4-[3-(3-dimethylaminopropyl)benzoyl]-1-(4-fluorophenyl)pyrazole;
5-amino-1-(4-fluorophenyl)-4-[3-(3-hydroxy-3-methylbutyl)benzoyl]pyrazole (90),
5-amino-1-(2,4-difluorophenyl)-4-[3-(3-pyridylethyl)benzoyl]pyrazole (91),
5-amino-1-(2,4-difluorophenyl)-4-[3-{3-(S,S-dioxo-thiomorpholin-4-yl)propyl}benzoyl]pyrazole (92),
5-amino-1-(4-fluorophenyl)-4-[3-{2-(1-hydroxycyclopentyl)ethyl}benzoyl]pyrazole (93), and 5-amino-1-(2,4-difluorophenyl)-4-[3-{2-(1-hydroxycyclopentyl)ethyl}benzoyl]pyrazole (94) respectively.

Example 3

5-Amino-1-(4-fluorophenyl)-4-[3-(2-(morpholin-4-yl)ethoxy}benzoyl]pyrazole hydrochloride (14)

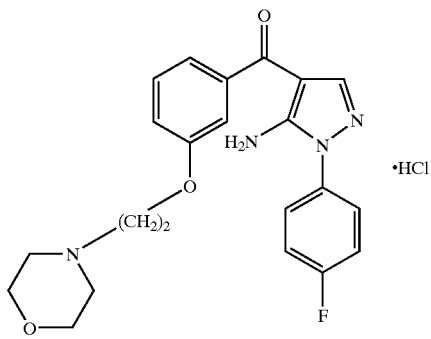

Step 1

A mixture of methyl 3-hydroxybenzoate (8.0 g, 56 mmol) and 4-(2-chloroethyl)morpholine hydrochloride (15.7 g, 84 mmol) and potassium carbonate (11.5 g, 83 mmol) in toluene (50 ml) was heated at reflux. After 4 days, the reaction mixture was cooled to room temperature and diluted with ethyl acetate. The organic layer was washed with water and then extracted with dilute hydrochloric acid. The acidic layer was separated, basified with 5 N sodium hydroxide and the product was extracted into ethyl acetate. The organics were removed in vacuo and the residue was purified by flash chromatography (elution gradient 3% acetone/methylene chloride) to give methyl 3-(morpholin-4-ylethoxy)benzoate (9.0 g) as an oil.

Step 2

Lithium diisopropylamide (18.8 ml, 37 mmol, 2.0 M solution in heptane/tetrahydrofuran/ethylbenzene) was added dropwise to a solution of acetonitrile (1.58 g, 37 mmol) in dry tetrahydrofuran (50 ml) at −78° C. After stirring the reaction mixture for 30 min., a solution of methyl 3-(2-morpholin-4-ylethoxy)benzoate in dry tetrahydrofuran (50 ml) was added dropwise over 10 min. After 15 min., water was added and the reaction mixture was allowed to warm to room temperature. The aqueous layer was separated and acidified with dilute hydrochloric acid to pH 7. The product was extracted into ethyl acetate and washed with water and brine and dried over magnesium sulfate. The organics were removed in vacuo to give 2-[3-(2-morpholin-4-ylethoxy)phenyl]acetonitrile (5.0 g) as an oil which was used in the next step without further purification.

Step 3

A mixture of 2-[3-(2-morpholin-4-ylethoxy)phenyl]acetonitrile (5.0 g) and N,N-diphenylformamidine (5.0 g, 25.5 mmol) in xylene (150 ml) was heated at 100° C. under a nitrogen atmosphere. After 3 h, the reaction mixture was cooled to room temperature and diluted with hexane to give 2-[3-(2-morpholin-4-ylethoxy)benzoyl]-3-phenylaminoacrylonitrile (5.0 g) as a solid.

Step 4

A mixture of 4-fluorophenylhydrazine (1.0 g, 6.8 mmol) and 2-[3-(2-morpholin-4-ylethoxy)-benzoyl]-3-phenylaminoacrylonitrile (2.0 g, 5.3 mmol) in ethanol (30 ml) was heated at reflux under a nitrogen atmosphere. After 6 h, the reaction mixture was cooled to room temperature and diluted with water. The product was extracted into ethyl acetate and the organic layer was washed with brine, dried over sodium sulfate and concentrated in vacuo. Purification by flash chromatography (elution gradient: CH$_2$Cl$_2$-3% MeOH/CH$_2$Cl$_2$) gave 5-amino-1-(4-fluorophenyl)-4-[3-(2-morpholin-4-ylethoxy)benzoyl]pyrazole which was converted to the hydrochloride salt (0.7 g, mpt. 191.6–192.5° C.).

Replacing 4-fluorophenylhydrazine in Step 4 above with:

2-fluorophenylhydrazine, and 2,6-dichlorophenylhydrazine, respectively were obtained:

5-amino-1-(2-fluorophenyl)-4-[3-(2-morpholin-4-ylethoxy)benzoyl]pyrazole (97), and 5-amino-1-(2,6-dichlorophenyl)-4-[3-(2-morpholin-4-ylethoxy)benzoyl]pyrazole (98).

Example 4

5-Amino-1-(4-fluorophenyl)-4-[3-(pyridin-3-yl)benzoyl]pyrazole (20)

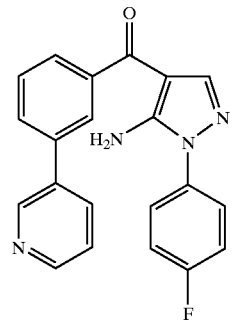

Step 1

A mixture of 5-amino-4-(3-bromobenzoyl)-1-(4-fluorophenyl)pyrazole (0.9 g, 2.5 mmol) [prepared as described in Example 1 above], pyridine-3-boronic acid, 1,3-propanediol cyclic ester (0.5 g, 3 mmol), potassium phosphate (0.8 g, 3.73 mmol) and tetrakistriphosphine palladium (0.3 g, 0.25 mmol) in dioxane (20 ml) was heated at 85° C. under argon. After 16 h, the reaction mixture was cooled to room temperature and poured into brine. The product was extracted into ethyl acetate, dried over sodium sulfate and filtered. The organic layer was removed in vacuo and the residue was purified by flash chromatography (elution gradient: 40–80% ethyl acetate/hexane) to give 5-amino-1-(4-fluorophenyl)-4-[3-(pyridin-3-yl)benzoyl]pyrazole (0.50 g) which was recrystallized from ethyl acetate (mpt. 222.2–223.0).

Treatment of 5-amino-1-(4-fluorophenyl)-4-[3-(pyridin-3-yl)benzoyl]-pyrazole with methyl iodide in ethylacetate gave 5-amino-1-(4-fluorophenyl)-4-[3-(N-methylpyridinium-3-yl)benzoyl]pyrazole iodide (59).

Substitution of 5-amino-4-(3-bromobenzoyl)-1-(4-fluorophenyl)pyrazole with 5-amino-4-(3-bromobenzoyl)-1-(2,4-difluorophenyl)pyrazole in Step 1 above followed by conversion to the hydrochloride salt gave 5-amino-1-(2,4-difluorophenyl)-4-[3-(pyridin-3-yl)benzoyl]pyrazole.HCl (99).

Example 5

5-Amino-4-[3-(2-aminosulfonylethyl)benzoyl]-1-(4-fluorophenyl)pyrazole (50)

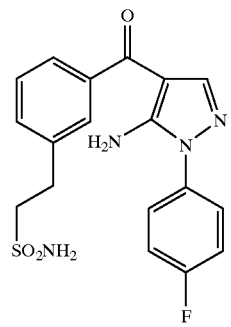

Step 1

A mixture of 5-amino-4-(3-bromobenzoyl)-1-(4-fluorophenyl)pyrazole (1.5 g, 4.14 mmol) [prepared as described in Example 1 above], vinylsulfonamide (1.33 g, 12.4 mmol), bis(triphenylphosphine)palladium chloride (0.3 g, 0.42 mmol) and triethylamine (6 ml, 43 mmol) in dimethylformamide (18 ml) was heated at 100° C. under argon. After 16 h, the reaction mixture was cooled to room temperature and poured into 1 N hydrochloric acid. The product was extracted into ethyl acetate, washed with brine, dried over sodium sulfate and filtered. The organic layer was removed in vacuo and the residue was purified by flash chromatography (elution gradient: 40–80% ethyl acetate/hexane) to give 5-amino-4-[3-(2-aminosulfonylethenyl)benzoyl]-1-(4-fluorophenyl)pyrazole which was recrystallized from a mixture of methanol/ethyl acetate/hexane to give 0.78 g of the desired product.

Step 2

A mixture of 5-amino-4-[3-(2-aminosulfonylethenyl)benzoyl]-1-(4-fluorophenyl)-pyrazole (2.1 g, 5.43 mmol) and palladium hydroxide (0.6 g) in methanol (150 ml) was shaken in a Parr apparatus under hydrogen atmosphere at 50 psi. After 4 days, the reaction mixture was filtered through Celite® and the filtrate was concentrated. The residue was purified by flash chromatography (elution gradient: 40–100% ethyl acetate/hexane) to give a crude product which was recrystallized from methanol/ethyl acetate/hexane to give 5-amino-4-[3-(2-aminosulfonylethyl)benzoyl]-1-(4-fluorophenyl)pyrazole (0.95 g, mpt. 170–170.4° C.) as a solid.

Replacement of vinylsulfonamide in Step 1 above with vinylmethylsulfone gave: 5-amino-4-[3-(2-methylsulfonylethyl)benzoyl]-1-(4-fluorophenyl)pyrazole (100).

Example 6

5-Amino-1-(4-fluorophenyl)-4-[3-(morpholin-4-ylmethylcarbonyl)-benzoyl]pyrazole (18)

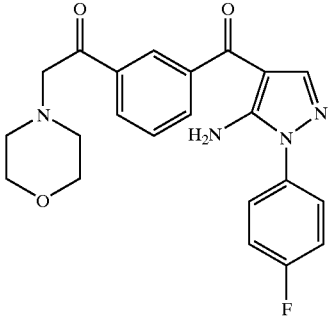

Step 1

A mixture of 5-amino-4-(3-bromobenzoyl)-1-(4-fluorophenyl)pyrazole (3.5 g, 9.7 mmol) [prepared as described in Example 1 above], tributyl-(1-ethoxyvinyl)tin (4.3 ml, 12.36 mmol) and tetrakis(triphenylphosphine)palladium (1.0 g, 0.87 mmol) in dimethylformamide (25 ml) was heated at 95° C. under argon. After 16 h, the reaction mixture was cooled to room temperature and 10% aqueous hydrochloric acid (25 ml) was slowly added. After 30 min., the reaction mixture was diluted with ethyl acetate and filtered through Celite®. The organic layer was separated and washed with brine, dried over sodium sulfate and concentrated in vacuo. The residue was purified by flash chromatography (elution gradient: 10–60% ethyl acetate/hexane) to give 5-amino-4-[3-(1-ethoxyvinyl)benzoyl]-1-(4-fluorophenyl)pyrazole which was dissolved in tetrahydrofuran (50 ml). 1 N hydrochloric acid (20 ml) was added and the reaction mixture was stirred at room temperature for 16 h. The organic layer was separated, washed with brine, dried over sodium sulfate and concentrated in vacuo. The crude product was purified by flash chromatography (elution gradient: 20–50% ethyl acetate/hexane) and then was recrystallized from a mixture of ethyl acetate/hexane to give 5-amino-4-[3-acetylbenzoyl]-1-(4-fluorophenyl)pyrazole (2.0 g).

Step 2

To a suspension of copper bromide (2.2 g, 9.85 mmol) in a (1:1) mixture of ethyl acetate/methylene chloride (100 ml) at reflux was added a solution of 5-amino-4-[3-acetylbenzoyl]-1-(4-fluorophenyl)pyrazole (1.6 g, 4.95 mmol) in methylene chloride (25 ml) under nitrogen. After 16 h, the reaction mixture was concentrated and the residue was partitioned between aqueous sodium bisulfite and ethyl acetate. The organic layer was separated, washed with brine, dried over sodium sulfate and concentrated in vacuo. The residue was purified by flash chromatography (elution gradient: 10–40% ethyl acetate/hexane) to give 5-amino-4-[3-(2-bromoacetyl)benzoyl]-1-(4-fluorophenyl)pyrazole (0.47 g) as a solid.

Step 3

To a solution of morpholine (0.25 ml, 2.79 mmol) in dimethylformamide (5 ml) was added a solution of 5-amino-4-[3-(2-bromoacetyl)benzoyl]-1-(4-fluorophenyl)pyrazole (0.22 g, 0.56 mmol) in dimethylformamide (5 ml). After 16 h, the reaction mixture was poured into brine and the product was extracted into ethyl acetate. The organic layer was separated, washed with brine, dried over sodium sulfate and concentrated in vacuo. The residue was purified by flash chromatography (elution gradient: ethyl acetate—10% methanol/ethyl acetate) to give 5-amino-1-(4-fluorophenyl)-4-[3-(morpholin-4-ylmethylcarbonyl)benzoyl]pyrazole (0.05 g) as a solid.

Example 7

5-Amino-1-(4-fluorophenyl)-4-[3-(2-hydroxyethyl)benzoyl]pyrazole (118)

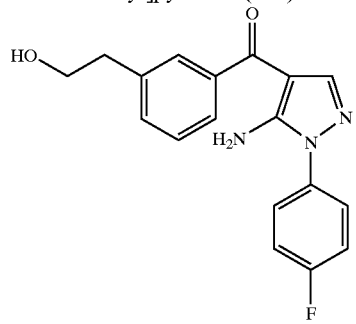

Step 1

To a solution of 3-bromophenylacetic acid (10 g, 46.5 mmol) in tetrahydrofuran (100 ml) at 0° C. was added diborane (70 ml, 1.0M solution in tetrahydrofuran). The reaction mixture was allowed to warm to room temperature. After 16 h, the reaction mixture was cooled to 0° C. and water was added dropwise (50 ml). The organic layer was separated and washed with brine, dried over sodium sulfate and concentrated in vacuo. The residue was purified by flash chromatography (elution gradient: 40–60% ethyl acetate/hexane) to give 3-(2-hydroxyethyl)bromobenzene (9.0 g).

Step 2

To a solution of 3-(2-hydroxyethyl)bromobenzene (4.0 g, 20 mmol) in methylene chloride (100 ml) at 0° C. was added a solution of tert-butyldimethylsilyl chloride (3.6 g, 24 mmol), dimethylaminopyridine (0.61 g, 5 mmol) and triethylamine (3.6 ml, 25.9 mmol). After 1 h, the reaction mixture was washed with brine, saturated ammonium chloride, dried over sodium sulfate and concentrated in vacuo. The residue was purified by flash chromatography (elution gradient: 0–10% hexane/ethyl acetate) to give 3-(2-tert-butyl-dimethylsiloxyethyl)bromobenzene (6.0 g).

Step 3

A mixture of ethyl (ethoxymethylene)cyanoacetate (26 ml, 154 mmol) and 4-fluorophenyl hydrazine (19.4 g, 154 mmol) in ethanol (125 ml) was heated at reflux. After 16 h, the reaction mixture was cooled to room temperature. The solid was filtered off and dried to give 5-amino-4-ethylcarboxy-1-(4-fluorophenyl)pyrazole (28 g) which was suspended in a mixture of 1 N lithium hydroxide (100 ml) and methanol (250 ml). The reaction mixture was heated at reflux. After 16 h, the reaction mixture was filtered through a sinter funnel and the filtrate was acidified with 2 N hydrochloric acid (65 ml). The solid was filtered off and dried to give 5-amino-4-carboxy-1-(4-fluorophenyl)pyrazole (21 g).

Step 4

A mixture of 5-amino-4-carboxy-1-(4-fluorophenyl)pyrazole (15 g, 68 mmol), aldrathiol-2 (14.9 g, 68 mmol) and triphenylphosphine (17.8 g, 68 mmol) in acetonitrile (2 l) was stirred at room temperature. After 16 h, the product was filtered off and dried to give 5-amino-1-(4-fluorophenyl)-4-(2-pyridylthiocarboxy)pyrazole (14 g).

Step 5

Into an oven dried flask containing magnesium turnings (0.386 g, 15.9 mmol) and tetrahydrofuran (10 ml) was added 3-(2-tert-butyldimethylsiloxyethyl)bromobenzene (5.0 g, 15.9 mmol) and the reaction mixture was heated at reflux. After 3 h, the reaction mixture was cooled to room temperature and 5-amino-1-(4-fluorophenyl)-4-(2-pyridylthiocarboxy)pyrazole (2.37 g, 7.6 mmol) was added and the stirring was continued for 16 h. The reaction mixture was concentrated in vacuo. The residue was dissolved in ethyl acetate and washed with aqueous ammonium chloride and brine and dried over sodium sulfate. The organics were removed in vacuo and the residue was purified by flash chromatography (elution gradient: 10–30% ethyl acetate/hexane) to give 5-amino-1-(4-fluorophenyl)-4-[3-(2-tert-butyldimethyl-siloxyethyl)benzoyl]pyrazole (1.20 g).

Step 6

To a solution of 5-amino-1-(4-fluorophenyl)-4-[3-(2-tert-butyldimethylsiloxyethyl)-benzoyl]pyrazole (1.2 g, 3.0 mmol) in tetrahydrofuran (25 ml) was added tetrabutylammonium fluoride (3.6 ml, 3.6 mmol, 1 M solution in tetrahydrofuran). After 1 h, the reaction mixture was poured into brine and the product was extracted into ethyl acetate. The organic layer was dried over sodium sulfate, filtered and concentrated in vacuo. The residue was purified by flash chromatography (elution gradient: 40–100% ethyl acetate/hexane) to give 5-amino-1-(4-fluorophenyl)-4-[3-(2-hydroxyethyl)benzoyl]pyrazole (0.8 g).

Example 8

Synthesis of 5-Amino-1-(4-fluorophenyl)-4-{3-[4-methylpiperazin-1-yl)ethyl)-benzoyl]pyrazole Dihydrochloride (31)

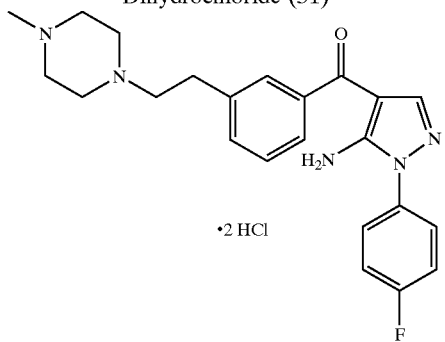

Step 1

To a solution of 5-amino-1-(4-fluorophenyl)-4-[3-(2-hydroxyethyl)benzoyl]pyrazole (0.8 g, 2.5 mmol) in pyridine (10 ml) was added methanesulfonyl chloride (0.29 ml, 3.7 mmol). After 2 h, the reaction mixture was poured into 2 N hydrochloric acid (40 ml) and the product was extracted into ethyl acetate. The organic layer was washed with brine, dried over sodium sulfate, filtered and concentrated in vacuo. The residue was purified by flash chromatography (elution gradient: 40–100% ethyl acetate/hexane) to give 5-amino-1-(4-fluorophenyl)-4-[3-(2-methanesulfonyloxyethyl)benzoyl]pyrazole (0.87 g).

Step 2

A mixture of 5-amino-1-(4-fluorophenyl)-5-[3-(2-methanesulfonyloxyethyl)-benzoyl]pyrazole (0.22 g, 0.55 mmol), N-methylpiperazine (0.18 ml, 1.64 mmol) and potassium carbonate (0.22 g, 1.64 mmol) in dimethylformamide (10 ml) was heated at 70° C. After 4 h, the reaction mixture was cooled to room temperature, poured into water and the product was extracted into ethyl acetate. The organic layer was washed with brine, dried over sodium sulfate, filtered and concentrated in vacuo. The residue was purified by flash chromatography (elution gradient: ethyl acetate—20% methanol/ethyl acetate) to 5-amino-1-(4-fluorophenyl)-4-{3-[4-methylpiperazin-1-yl)benzoyl]pyrazole which was converted to the hydrochloric salt (mpt. 272.9–273.9).

Example 9

5-Amino-4-[3-(2-aminoethyl)benzoyl]-1-(4-fluorophenyl)-pyrazole Hydrochloride (47)

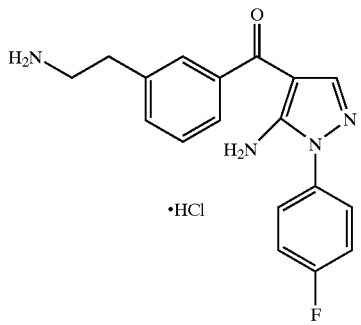

Step 1

A mixture of 5-amino-1-(4-fluorophenyl)-4-[3-(2-methanesulfonyloxyethyl)-benzoyl]pyrazole (0.40 gm, 0.99 mmol), sodium azide (0.19 ml, 2.97 mmol) and potassium carbonate (0.41 g, 2.97 mmol) in dimethylformamide (15 ml) was stirred at room temperature. After 16 h, the reaction mixture was poured into brine and the product was extracted into ethyl acetate. The organic layer was dried over sodium sulfate, filtered and concentrated in vacuo. The residue was purified by flash chromatography (elution gradient: 20–50% ethyl acetate/hexane) to 5-amino-1-(4-fluorophenyl)-4-[3-(2-azidoethyl)benzoyl]pyrazole (0.32 g).

Step 2

To a solution of 5-amino-1-(4-fluorophenyl)-4-[3-(2-azidoethyl)benzoyl]pyrazole (0.31 g, 0.9 mmol) in tetrahydrofuran (15 ml) was added triphenylphosphine (3.55 g, 1.36 mmol). After 48 h, the reaction mixture concentrated in vacuo. The residue was dissolved in 2 N sodium hydroxide and the product was extracted into ethyl acetate. The organic layer was dried over sodium sulfate, filtered and concentrated in vacuo. The product was converted to its hydrochloride salt and recrystallized from a mixture of methanol-ethyl acetate to give 5-amino-4-[3-(2-aminoethyl)benzoyl]-1-(4-fluorophenyl)pyrazole hydrochloride salt (0.22 g).

Example 10

5-Amino-4-[3-(tert-butoxycarbonylmethyloxy)benzoyl]-1-(4-fluorophenyl)pyrazole

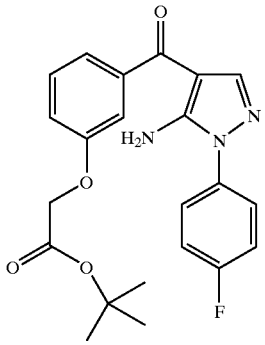

Step 1

Into an oven dried flask containing magnesium turnings (0.408 g, 17 mmol) and tetrahydrofuran (10 ml) was added 3-bromoanisole (3.1 g, 17 mmol) and the reaction mixture was heated at reflux. After 2 h, the reaction mixture was cooled to room temperature and 5-amino-1-(4-fluorophenyl)-4-(2-pyridylthiocarboxy)pyrazole (1.5 g, 4.8 mmol) was added and the stirring was continued for 1 h. The reaction mixture was quenched with water and the product was extracted into ethyl acetate. The organic layer was washed with aqueous ammonium chloride and brine and dried over sodium sulfate. The organics were removed in vacuo and the residue was filtered and washed with hexane to give 5-amino-1-(4-fluorophenyl)-4-(3-methoxybenzoyl)pyrazole (1.20 g).

Step 2

To an ice-cooled solution of 5-amino-1-(4-fluorophenyl)-4-(3-methoxybenzoyl)-pyrazole (3.0 g, 10.0 mmol) in methylene chloride (25 ml) was added boron tribromide (51 ml, 51 mmol, 1 M solution in methylene chloride). After 1 h, the reaction mixture was poured into brine and the product was extracted into ethyl acetate. The organic layer was dried over sodium sulfate, filtered and concentrated in vacuo to give 5-amino-1-(4-fluorophenyl)-4-[3-hydroxybenzoyl]pyrazole (2.4 g).

Step 3

A mixture of 5-amino-1-(4-fluorophenyl)-4-[3-hydroxybenzoyl]pyrazole (1.0 g, 3.3 mmol), tert-butyl bromoacetate (1.4 g, 7.2 mmol) and potassium carbonate (1 g, 7.2 mmol) in acetonitrile was heated at 70° C. overnight. The reaction mixture was cooled, diluted with ethyl acetate and filtered. The filtrate was concentrated in vacuo and the residue was purified by flash chromatography (elution gradient; 10% acetone/hexane) to give 5-amino-4-[3-(tert-butoxycarbonylmethyloxy)benzoyl]-1-(4-fluorophenyl)pyrazole (1.2 g) as a solid.

Example 11

5-Amino-4-[3-carboxymethyloxy)benzoyl]-1-(4-fluorophenyl)-pyrazole (119)

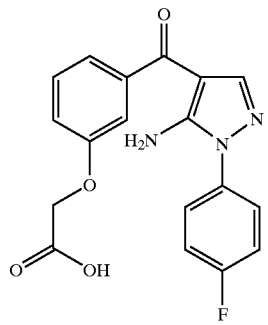

Step 1

A mixture of 5-amino-4-[3-(tert-butoxycarbonylmethyloxy)benzoyl]-1-(4-fluorophenyl)pyrazole (1.0 g, 3.3 mmol) and trifluoroacetic acid (15 ml, 194 mmol) in methylene chloride (15 ml) was stirred overnight at room temperature. The organics were removed in vacuo and the residue was dissolved in toluene. The solution was concentrated and the residue was triturated between ethyl acetate and hexane to give 5-amino-4-[3-(carboxymethyloxy)benzoyl]-1-(4-fluorophenyl)pyrazole (0.8 g) as a solid.

Example 12

5-Amino-1-(4-fluorophenyl)-4-[3-(methylaminocarbonylmethyloxy)benzoyl]pyrazole (34)

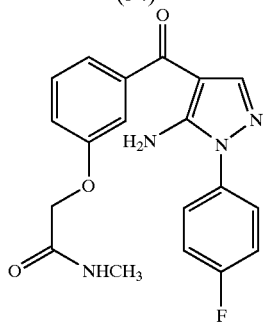

Step 1

To a solution of 5-amino-4-[3-(carboxymethyloxy)benzoyl]-1-(4-fluorophenyl)pyrazole (0.5 g, 1.43 mmol) in tetrahydrofuran (10 ml) was added carbonyl diimidazole (0.3 g, 1.85 mmol) and the reaction mixture was heated at 60° C. After 1 h, methylamine (10 ml, 5 mmol, 0.5 M solution in tetrahydrofuran) was added and reaction was continued at 60° C. overnight. The reaction mixture was cooled and diluted with ethyl acetate. The organic layer was separated and washed with brine and dried over sodium sulfate. The organics were removed in vacuo and the residue was purified by flash chromatography (elution gradient: 20–30% acetone/hexane) to give 5-amino-1-(4-fluorophenyl)-4-[3-(methylaminocarbonyl-methyloxy)benzoyl]pyrazole (0.25 g, mpt. 195.6–196.3° C.) as a solid.

Proceeding as described in Example 12 above, but substituting methylamine with: morpholine gave 5-amino-1-(4-fluorophenyl)-4-[3-(morpholin-4-ylcarbonylmethyloxy)benzoyl]pyrazole (35).

Example 13

5-Amino-1-(4-fluorophenyl)-4-[3-{3-morpholin-4-yl)propylamino}benzoyl]pyrazole (48)

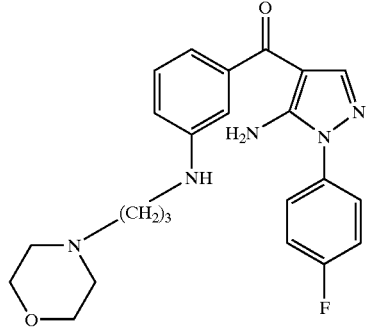

Step 1

Benzoylacetonitrile (14.5 g, 10 mmol) was added to cold fuming nitric acid (50 ml) portionwise over 10 min. The reaction mixture was stirred for 15 min., and then poured into ice. The solid was filtered off and recrystallised from ethanol to give 2-(3-nitrobenzoyl)acetonitrile (5.4 g) as a brown solid.

Step 2

A mixture of 2-(3-nitrobenzoyl)acetonitrile (13.75 g, 72.3 mmol) and N,N-diphenylformamidine (14.2 g, 72.3 mmol) in xylene (200 ml) was heated at reflux under nitrogen atmosphere. After 3 h, the reaction mixture was cooled to room temperature and diluted with xylenes to give 2-(3-nitrobenzoyl)-3-phenylaminoacrylonitrile (15.7 g) as a yellow solid.

Step 3

A mixture of 4-fluorophenylhydrazine (2.24 g, 15.57 mmol) and 2-(3-nitrobenzoyl)-3-phenylaminoacrylonitrile (4.15 g, 14.16 mmol) in ethanol (50 ml) was heated at reflux under nitrogen atmosphere. After 1 h, the reaction mixture was cooled to room temperature and stirred for an additional 3 h. The solid was filtered and dried to give 5-amino-1-(4-fluorophenyl)-4-(3-nitrobenzoyl)pyrazole (4.5 g) as a solid.

Step 4

A mixture of 5-amino-1-(4-fluorophenyl)-4-(3-nitrobenzoyl)pyrazole (4.0 g, 24.52), Fe powder (3.84 g, 68 mmol) and ammonium chloride (3.84, 71.78 mmol) in ethanol (135 ml) and water (64 ml) was heated at reflux under nitrogen atmosphere. After 1 h, the reaction mixture was cooled to room temperature and stirred overnight. The reaction mixture was filtered through Celite® and the filtrate was concentrated in vacuo. The residue was partitioned between water and ethyl acetate. The organic layer was separated and washed with brine, dried over sodium sulfate and concentrated in vacuo to give 5-amino-4-(3-aminobenzoyl)-1-(4-fluorophenyl)pyrazole (3.5 g) as a solid.

Step 5

5-amino-4-(3-aminobenzoyl)-1-(4-fluorophenyl)pyrazole (0.5 g, 1.6 mmol), 1-bromo-3-chloropropane (0.26 g, 1.6 mmol) and cesium carbonate (0.52 g, 1.6 mmol) in dimethylformamide (25 ml) was heated at 80° C. After 2 days, the reaction mixture was cooled to room temperature and diluted with ethyl acetate. The organic layer was washed with brine, dried over sodium sulfate and concentrated in vacuo. The residue was purified by flash chromatography (elution gradient: 20% acetone/hexanes) to give 5-amino-4-[3-(3-chloropropylamino)benzoyl]-1-(4-fluorophenyl)pyrazole (0.2 g) as a solid.

Step 6

A mixture of 5-amino-4-[3-(3-chloropropylamino)benzoyl]-1-(4-fluorophenyl)pyrazole (0.05 g, 0.13 mmol), morpholine (0.1 ml, 1.1 mmol), potassium carbonate (0.1 g) and potassium iodide (0.1 g) in acetonitrile (3 ml) was heated at reflux. After 2 days, the reaction mixture was poured into brine and the product was extracted into ethyl acetate. The organic layer was separated, washed with brine, dried over sodium sulfate and concentrated in vacuo. The residue was purified by flash chromatography (elution gradient: 3% MeOH/CH$_2$Cl$_2$) to give 5-amino-1-(4-fluorophenyl)-4-[3-{3-(morpholin-4-yl)propylamino}benzoyl]pyrazole as a solid.

Example 14

5-Amino-1-(4-fluorophenyl)-4-[3-{2-(piperidin-1-yl)ethoxy}benzoyl]pyrazole HCl salt (81)

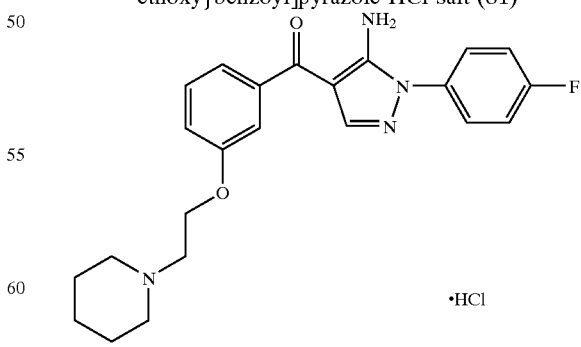

Step 1

5-Amino-1-(4-fluorophenyl)-4-[3-hydroxybenzoyl]pyrazole, from Example 10, step 2, 1.5 g, 5.05 mmol) was combined with toluene (50 mL). 2-bromoethanol (1.79 mL, 25.23 mmol) was added and then the reaction mixture was cooled to 0° C. Triphenylphosphine (5.425 g, 20.69 mmol) and diethyl azodicarboxylate (3.26 mL, 20.69 mmol) was then added. The reaction was allowed to warm to room temperature. After stirring for 16 hours, the reaction was quenched with a saturated aqueous solution of NH$_4$Cl, extracted with ethyl acetate, dried (MgSO$_4$), filtered, and concentrated under vacuum. The product (5-amino-1-(4-fluorophenyl)-4-[3-(2-bromoethoxy)benzoyl]pyrazole) was purified by column chromatography on silica gel using 40:1 CH$_2$Cl$_2$/MeOH then stirred with ether for 20 minutes, filtered and dried to give 0.785 g of product.

Step 2

5-amino-1-(4-fluorophenyl)-4-[3-(2-bromoethoxy)benzoyl]pyrazole (0.6 g, 1.48 mmol) was combined with piperidine (1.47 mL, 14.8 mmol) and ethanol (10 mL) and heated at reflux for 16 hrs. The reaction mixture was concentrated under vacuum. The resulting residue was partitioned between a saturated aqueous solution of NaHCO$_3$ and ethyl acetate and extracted three times with ethyl acetate. The organic extracts were dried (MgSO$_4$), filtered, concentrated under vacuum and purified by column chromatography on silica gel using 16:1 CH$_2$Cl$_2$/MeOH. Dissolving the product in ethyl acetate then adding hydrochloric acid (1.0M, 1.0 equivalent) formed the hydrochloric salt which was filtered and dried to give 0.413 g of 5-amino-1-(4-fluorophenyl)-4-[3-{2-(piperidin-1-yl)ethoxy}benzoyl]pyrazole.HCl (mpt 210.2–211.2° C.).

Proceeding as in Step 2 but replacing piperidine with diethanolamine, dimethylamine, N-methylpiperazine, 2-aminoethanol, bis(2-methoxyethyl)amine, diethylamine, methylamine, ammonia, and 3-oxypyridazine the following compounds were obtained.

| Mole Structure | CPD # | HRMS MW | Melting Point |
|---|---|---|---|
| 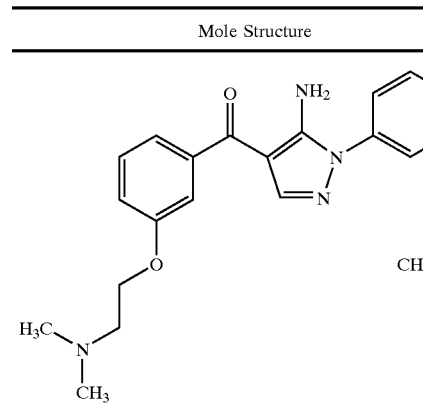 | 121 | 368.41 | 184.5–190 |
| 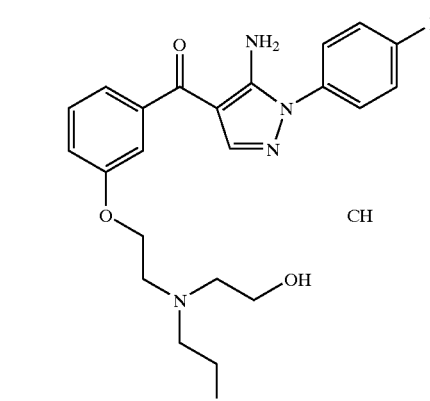 | 39 | 464.922 | 160.3–160.8 |
| 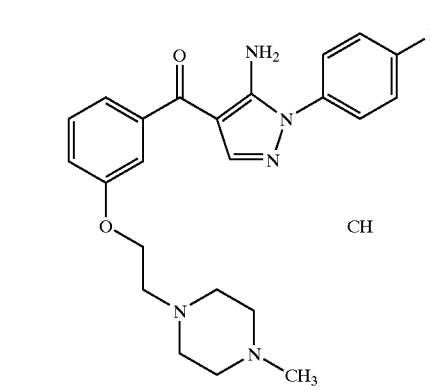 | 122 | 494.95 | 238.0–258.0 |

-continued

| Mole Structure | CPD # | HRMS MW | Melting Point |
|---|---|---|---|
| (structure) | 123 | 425.4 | 217.1–218.0 |
| (structure) | 124 | 506.49 | 86.5–93.5 |
| (structure) | 125 | 440.13 | 137.8–139.8 |
| (structure) | 126 | 396.25 | 204.9–210.3 |

| Mole Structure | CPD # | HRMS MW | Melting Point |
|---|---|---|---|
| (structure 127) | 127 | 376.817 | 231.5–232.5 |
| (structure 128) | 128 | 419.414 | 174.5–176.0 |

Example 15

5-Amino-1-(4-fluorophenyl)-4-[3-(pyridin-2-ylmethoxy)benzoyl]pyrazole (82)

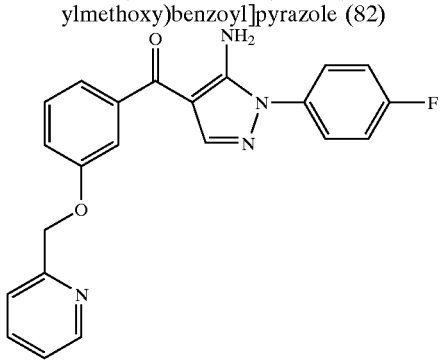

5-Amino-1-(4-fluorophenyl)-4-[3-hydroxybenzoyl] pyrazole, from Example 10, step 2, (0.5 g, 1.68 mmol), 2-pyridylcarbinol (0.81 mL, 8.41 mmol), triphenylphosphine (1.81 g, 6.9 mmol), and diethylazodicarboxylate (1.09 mL, 6.9 mmol)) were combined in toluene (50 mL). The reaction mixture was stirred for 16 hours then quenched with a saturated aqueous solution of NH₄Cl and extracted three times with ethyl acetate. The product was then extracted from the ethyl acetate into a 10% aqueous solution of HCl. The aqueous layer was then neutralized with NaOH and extracted with ethyl acetate. The organic extracts were dried (MgSO₄), filtered, and concentrated under vacuum. The residue was purified by column chromatography on silica gel using 1:1 hexane/ethyl acetate to give 0.165 g of 5-amino-1-(4-fluorophenyl)-4-[3-(pyridin-2-ylmethoxy)benzoyl]pyrazole (mpt. 176.1–177.3° C.).

Replacing 2-pyridylcarbinol with glycolic acid, 1-(2-hydroxyethyl)-2-pyrrolidinone and 4-hydroxypiperidine gave the following compounds.

| Structure | CPD # | HRMS MWt | M. Pt. |
|---|---|---|---|
| (structure 119) | 119 | 355.324 | 215.9–216.2 |

| Structure | CPD # | HRMS MWt | M. Pt. |
|---|---|---|---|
| (structure 129) | 129 | 412.03 | |
| (structure 130) | 130 | 416.882 | 195.0–220.0 |

Example 16

5-Amino-1-(4-fluorophenyl)-4-[3-isopropylaminocarbonyloxybenzoyl]pyrazole (83)

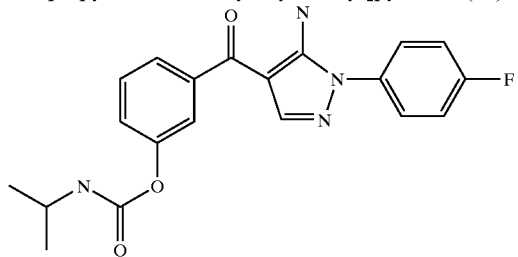

5-Amino-1-(4-fluorophenyl)-4-[3-hydroxybenzoyl] pyrazole, step 2, (0.30 g, 1.01 mmol) was combined with $K_2CO_3$ (0.418 g, 3.03 mmol) and THF (6 mL). The mixture was cooled in an ice bath and then isopropyl isocyanate (0.12 mL, 1.21 mmol) was added. The reaction was allowed to warm to room temperature and stirred for 16 hours. The reaction mixture was quenched with water, extracted into ethyl acetate, dried ($MgSO_4$), filtered, and concentrated to dryness. The residue was stirred in methanol and dichloromethane for one hour then filtered to give 0.118 g of 5-amino-1-(4-fluorophenyl)-4-[3-isopropylaminocarbonyloxybenzoyl]pyrazole (mpt. 225.2–230.1° C.).

Replacing isopropyl isocyanate with ethyl isocyanate was made 5-amino-1-(4-fluorophenyl)-4-[3-ethylaminocarbonyloxybenzoyl]pyrazole (84). Mpt. 201.2–202.8° C.

Example 17

5-Amino-1-(4-fluorophenyl)-4-[3-iodo benzoyl] pyrazole

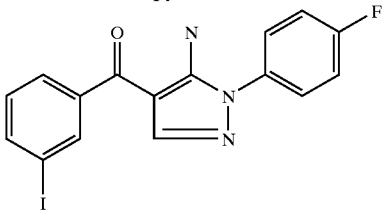

Step 1 n-Butyllithium (30.5 ml, 76 mmol, 2.5 M solution in hexane) was added dropwise to a cooled (0° C.) solution of diisopropylamine (10.6 ml, 76 mmol) in 10 ml dry tetrahydrofuran. Once addition was complete, the solution was kept at 0° C. for 10 minutes and was then cooled to −50° C. This cold LDA solution was then added to a −50° C. solution of acetonitrile (2.37 ml, 45.3 mmol) and ethyl 4-iodobenzoate (10.0 g, 36.2 mmol) in dry tetrahydrofuran (18 ml). Once addition was complete, the reaction was stirred at −50° C. for 3 hours and was subsequently warmed to 0° C. Saturated ammonium chloride was added (20 ml) and the reaction mixture was allowed to warm to room temperature. The product was extracted into ether and washed with 1N hydrochloric acid (50 ml). The organics were washed with brine (50 ml), dried over $MgSO_4$ and then concentrated in vacuo to a red oil. The oil was purified through a small plug of silica gel using 3:1–2:1 hexanes/ethyl acetate as eluent. Concentration of the column fractions in vacuo gave 2-(3-iodobenzoyl)-acetonitrile (8.3 g) as a yellow oil.

Step 2

A mixture of 2-(3-iodobenzoyl)acetonitrile (36.2 g, 133.5 mmol) and N,N-diphenylformamide (26.2 g, 133.5 mmol) in toluene (200 ml) was heated at reflux under a nitrogen atmosphere. After 8 h, the reaction mixture was cooled to room temperature and diluted with ether (200 ml) to give 2-(3-iodobenzoyl)-3-phenylaminoacrylonitrile (31.2 g) as a solid.

Step 3

A mixture of 4-fluorophenylhydrazine (26.6 g, 211 mmol) and 2-(3-iodobenzoyl)-3-phenylaminoacrylonitrile (79 g, 211 mmol) in ethanol (400 ml) was heated at reflux under a nitrogen atmosphere. After 30 minutes, the reaction mixture was cooled to room temperature, diluted with hexane to give 5-amino-4-(3-iodobenzoyl)-1-(4-fluorophenyl)pyrazole (75.1 g) as a solid.

Replacing 4-fluorophenylhydrazine with 4-methylphenyllhydrazine, 3-methoxyphenylhydrazine, 4-sulfamoylphenylhydrazine, 2,4-dimethylphenylhydrazine, 2-methylphenylhydrazine, 4-chloroo-2-methylphenylhydrazine, 4-methylsulfonylphenylhydrazine, 2-ethylphenylhydrazine, and 2,4-difluorophenylhydrazine in Step 3 above gave respectively:

5-amino-4-(3-iodobenzoyl)-1-(4-methylphenyl)pyrazole,
5-amino-4-(3-iodobenzoyl)-1-(3-methoxyphenyl)pyrazole,
5-amino-4-(3-iodobenzoyl)-1-(4-sulfamoylphenyl) pyrazole,
5-amino-4-(3-iodobenzoyl)-1-(2,4-dimethylphenyl) pyrazole,
5-amino-4-(3-iodobenzoyl)-1-(2-methylphenyl)pyrazole,
5-amino-4-(3-iodobenzoyl)-1-(4-chloro-2-methylphenyl) pyrazole,
5-amino-4-(3-iodobenzoyl)-1-(4-methylsulfonylphenyl) pyrazole,
5-amino-4-(3-iodobenzoyl)-1-(2-ethylphenyl)pyrazol, and
5-amino-4-(3-iodobenzoyl)-1-(2,4-difluorophenyl)pyrazole.

Example 18

5-Amino-1-(4-fluorophenyl)-4-[3-(1,2-dihydroxyethyl)benzoyl]pyrazole (85)

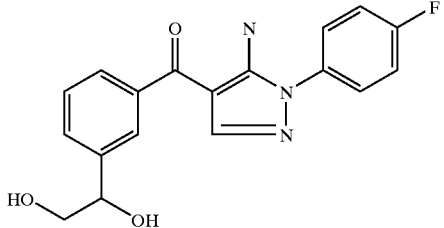

Step 1

To a solution of 5-amino-1-(4-fluorophenyl)-4-[3-iodobenzoyl]pyrazole (10 g, 24.6 mmol) in 100 ml dimethylformamide was added vinyltributytin (8.57 g, 27.0 mmol) and tetrakistriphenylphosphine palladium (0) (1.42 g, 1.23 mmol). The resulting solution was degassed with argon and subsequently warmed to 100° C. for 12 hours.

The reaction was cooled to room temperature and was poured into 500 ml distilled water and was extracted 3× 100 ml 1:1 ether/ethyl acetate. The organics were washed with brine (150 ml), dried over MgSO₄ and then concentrated in vacuo to a brown oil. The oil was purified by flash column chromatography using 5:1–4:1 hexanes/ethyl acetate to remove impurities and 3:1–2:1 hexanes/ethyl acetate to elute the desired product. Concentration of the column fractions in vacuo gave 5-amino-1-(4-fluorophenyl)-4-[3-vinylbenzoyl]pyrazole (4.48 g) as a white solid.

Step 2

To a suspension of 5-amino-1-(4-fluorophenyl)-4-[3-vinylbenzoyl]pyrazole (4.48 g, 13.95 mmol) in 50 ml t-butanol was added N-methylmorpholine N-oxide (1.79 g, 15.35 mmol) in 50 ml distilled water. To this mixture at room temperature was added a solution of 2.5% osmium tetraoxide in t-butanol (5.25 ml, 0.42 mmol). After 5 hours, the homogenous reaction was diluted with ethyl acetate (25 ml) and the organics were separated and washed with brine (25 ml), dried over MgSO₄ and then concentrated in vacuo to a brown oil. The oil was purified by flash column chromatography using 1:1 hexanes/ethyl acetate to remove impurities and ethyl acetate to elute the desired product. Concentration of the column fractions in vacuo gave 5-amino-1-(4-fluorophenyl)-4-[3-(1,2-dihydroxyethyl)benzoyl]pyrazole (4.48 g) as a white foam. The foam was triturated to a solid from hexanes (2.36 g).

Replacing 5-amino-1-(4-fluorophenyl)-4-[3-iodobenzoyl]pyrazole in Step 1 above with:
5-amino-1-(2,4-difluorophenyl)-4-[3-iodobenzoyl]pyrazole and
5-amino-1-(2-methylphenyl)-4-[3-iodobenzoyl]pyrazole, gave respectively
5-amino-1-(2,4-difluorophenyl)-4-[3-(1,2-dihydroxyethyl) benzoyl]pyrazole (103) and
5-amino-1-(2-methylphenyl)-4-[3-(1,2-dihydroxyethyl) benzoyl]pyrazole (109).

Example 19

5-Amino-1-(2,4-difluorophenyl)-4-[3-(1-piperidinylmethyl)benzoyl]pyrazole (86)

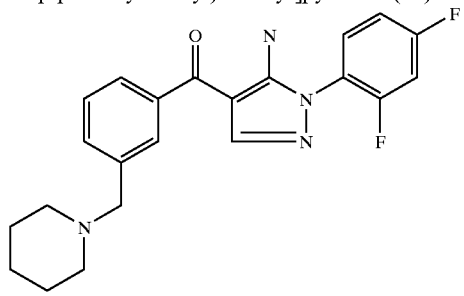

Step 1

To a suspension of 5-amino-1-(2,4-difluorophenyl)-4-[3-(1,2-dihydroxyethane)benzoyl]pyrazole (10.1 g, 28 mmol) in 100 ml t-butanol was added 100 ml distilled water and sodium periodate (18.06 g, 84 mmol). After 2 hours, the solid precipitate was collected by vacuum filtration and was washed with 300 ml distilled water and dried in vacuo to give 8.28 g of 5-amino-1-(2,4-difluorophenyl)-4-[3-formylbenzoyl]pyrazole as a white solid.

Step 2

To a solution of 5-amino-1-(2,4-difluorophenyl)-4-[3-formylbenzoyl]pyrazole (0.3 g, 0.92 mmol), piperidine (0.1 ml, 1.0 mmol), acetic acid (0.05 ml) in 1,2-dichloroethane (5 ml) was added sodium triacetoxyborohydride (0.29 g, 1.37 mmol). After stirring at room temperature for 12 hours, the reaction was diluted with 10% hydrochloric acid and ethyl acetate (10 ml). The aqueous layer was separated and neutralized to pH 9 with sodium hydroxide and was then extracted with ethyl acetate. The combined organics were separated and washed with brine (25 ml), dried over MgSO₄ and then concentrated in vacuo to a brown oil. The oil was purified by flash column chromatography using 1:1 hexanes/ ethyl acetate to remove impurities and ethyl acetate to elute the desired product. Concentration of the column fractions in vacuo gave 5-amino-1-(4-fluorophenyl)-4-[3-(1-piperidinylmethyl)-benzoyl]pyrazole as an oil (0.211 g). The compound was triturated to a solid from hexanes/ethyl acetate.

Replacing piperidine in Step 2 above with:
morpholine,
N-methylpiperazine,
4-hydroxypiperidine,
2-aminopyridine,
3-aminopyridine,
4-methylimidazole,
3-aminopyrazole, and
2-methylimidazole;
the following compounds were obtained

| Structure | CPD # | HRMS MW | MPt |
|---|---|---|---|
| 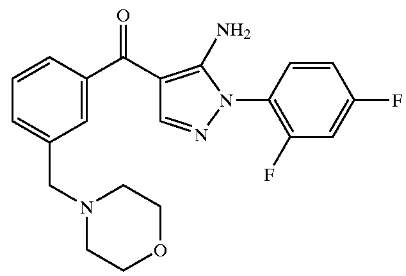 | 131 | 398.411 | 127.3–128.5 |
| 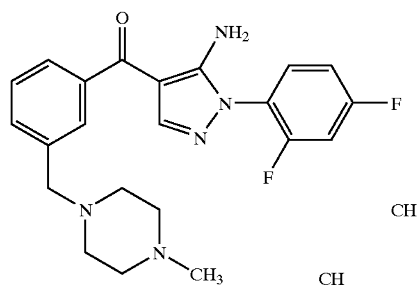 | 132 | 484.376 | 238.2–236.6 |
| 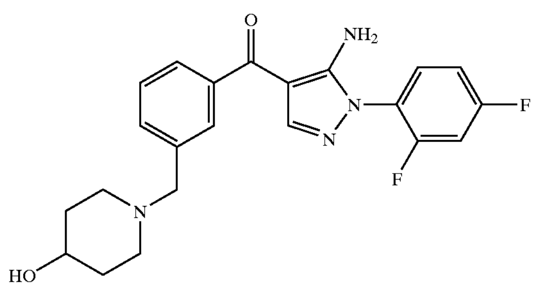 | 133 | 412.438 | 141.5–145.5 |
| 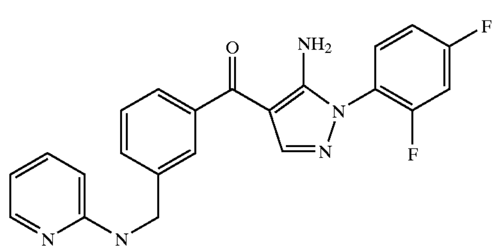 | 134 | 405.406 | |
| 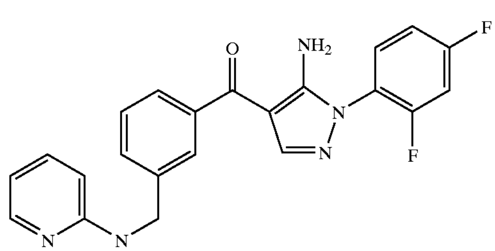 | 135 | 405.406 | |

| Structure | CPD # | HRMS MW | MPt |
|---|---|---|---|
| 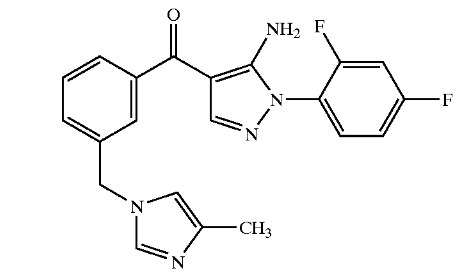 | 136 | 393.395 | |
| 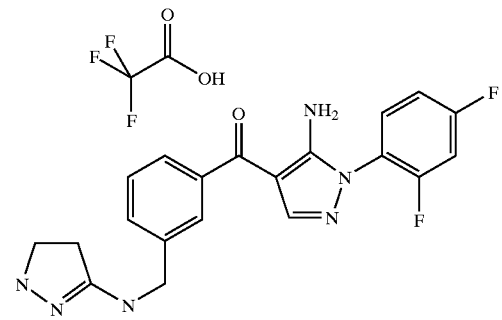 | 137 | 508.405 | |
| 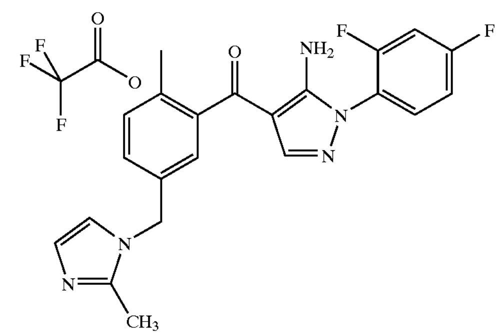 | 138 | 507.417 | |

Example 20

5-Amino-1-(3-methylphenyl)-4-[3-{N-oxidopyridin-3-yl}]benzoyl]pyrazole (70)

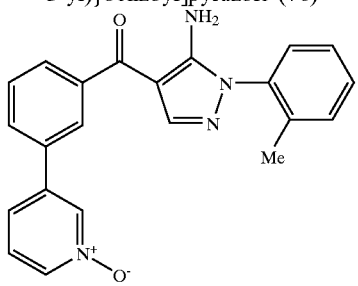

A mixture of 5-amino-4-(3-iodobenzoyl)-1-(2-methylphenyl)pyrazole, from Example 17 (0.98 g, 2.4 mmol), pinacol diboron (0.68 g, 2.7 mmol), [1,1'-bis(diphenylphoshino)ferrocene]dichloropalladium (0.2 g, 24 mmol) and potassium acetate (0.72 g, 7.3 mmol) in DMF (10 ml) was heated at 80 degrees, under argon. After 2 h, the reaction mixture was cooled to room temperature and 3-bromopyridine N-oxide (0.47 g, 2.7 mmol), [1,1'-bis(diphenylphosphino)ferrocene]dichloropalladium (0.2 g, 0.24 mmol) and 2 M sodium carbonate (6.1 ml, 12.2 mmol) was added and heated to 80 degrees. After 16 h, the reaction mixture was cooled to room temperature, poured into brine and the product extracted into ethyl acetate. The organic layer was dried over sodium sulfate, filtered and then the solution was evaporated to dryness. The residue was purified by flash chromatography (gradient elution: ethyl acetate to 20% methanol/ethyl acetate) to give, after recrystallization from methanol/ethyl acetate/hexane, 5-amino-1-(3-methylphenyl)-4-[3-(N-oxidopyridin-3-yl)benzoyl]pyrazole (0.57 g, mpt. 190.5–191.2).

Replacing 5-amino-4-(3-iodobenzoyl)-1-(2-methylphenyl)pyrazole/3-bromopyridine N-oxide with:

5-amino-4-(3-iodobenzoyl)-1-(4-methylphenyl)pyrazole/3-bromopyridine, 5-amino-4-(3-iodobenzoyl)-1-(3-methoxyphenyl)pyrazole/3-bromopyridine, 5-amino-4-(3-iodobenzoyl)-1-(4-sulfamoylphenyl)pyrazole/3-bromopyridine, 5-amino-4-(3-iodobenzoyl)-1-(2,4-dimethylphenyl)pyrazole/3-bromopyridine, 5-amino-4-(3-iodobenzoyl)-1-(2-methylphenyl)pyrazole/3-bromopyridine-N-oxide, 5-amino-4-(3-iodobenzoyl)-1-(4-chloro-2-methylphenyl)
pyrazole/3-bromopyridine, 5-amino-4-(3-iodobenzoyl)-1-(4-methylsulfonylphenyl)
pyrazole/3-bromopyridine, 5-amino-4-(3-iodobenzoyl)-1-(2-ethylphenyl)pyrazole/3-
bromopyridine, and 5-amino-4-(3-iodobenzoyl)-1-(2,4-difluorophenyl)
pyrazole/2-bromoimidazole, gave respectively the following compounds (as their hydrochloride salts as appropriate):

5-amino-1-(4-methylphenyl)-4-[3-(pyridin-3-yl)benzoyl]
pyrazole (65), 5-amino-1-(2-methoxyphenyl)-4-[3-(pyridin-3-yl)
benzoyl]pyrazole (66), 5-amino-1-(4-sulfamoylphenyl)-4-[3-(pyridin-3-yl)
benzoyl]pyrazole (68), 5-amino-1-(2,4-dimethylphenyl)-4-[3-(pyridin-3-yl)
benzoyl]pyrazole (69), 5-amino-1-(2-methylphenyl)-4-[3-(N-oxidopyridin-3-yl)
benzoyl]pyrazole (70), 5-amino-1-(4-chloro-2-methylphenyl)-4-[3-(pyridin-3-
yl)benzoyl]pyrazole (73), 5-amino-1-(4-methylsulfonylphenyl)-4-[3-(pyridin-3-yl)
benzoyl]pyrazole (75), 5-amino-1-(2-ethylphenyl)-4-[3-(pyridin-3-yl)benzoyl]
pyrazole (76), and 5-amino-1-(2,4-difluorophenyl)-4-[3-(imidazol-2-yl)
benzoyl]pyrazole (77).

Example 21

5-Amino-1-(2,4-difluorophenyl)-4-[N-oxidopyridin-
3-yl)benzoyl]pyrazole (60)

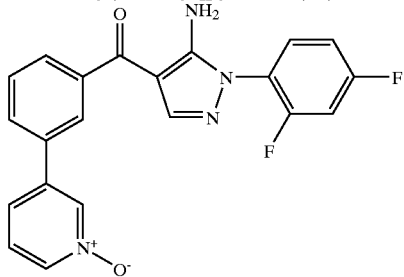

To a solution of 5-amino-1-(2,4-difluorophenyl)-4-[3-(pyridin-3-yl)benzoyl]pyrazole (4.6 g, 12.2 mmol) in dichloromethane (100 ml) was added 3-chloroperoxybenzoic acid (5.6 g, 18.3 mmol) and the mixture was stirred at room temperature. After 4 h, a solution of 10% aqueous sodium sulfite (50 ml) was added. After 0.5 h, the organic layer was separted, washed with brine, dried over sodium sulfate and filtered. The filtrate was concentrated to dryness and the residue purified by flash chromatography (gradient elution: ethyl acetate to 30% methanol/ethyl acetate)to give, after recrystalliztion from methanol, 5-amino-1-(2,4-difluorphenyl)-4-[3-N-oxidopyridin-3-yl)benzoyl]pyrazole (1.3 g, Mpt. 251.1–251.7° C.).

Example 22

5-Amino-1-(2,4-difluorophenyl)-4-[pyridin-4-yl)
benzoyl]pyrazole (61)

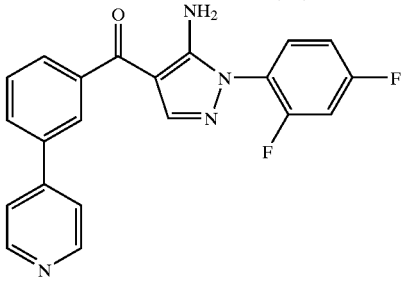

A mixture of 5-amino-4-(3-bromobenzoyl)-1-(2,4-difluorophenyl)pyrazole (0.93 g, 2.5 mmol), 4-tributylstannylpyridine (1.0 g, 2.7 mmol) and bis (triphenylphosphine)palladium chloride (0.17 g, 2.5 mmol) in DMF (15 ml) was heated at 100 degrees under argon. After 16 h, the reaction mixture was cooled to room temperature and a solution of 10% aqueous potassium flouride (30 ml) was added. After 1 h, the reaction mixture was poured into brine, extracted with ethyl acetate, dried over sodium sulfate, filtered and concentrated to dryness. The residue was purified by flash chromatography (gradient elution: 50–100% ethyl acetate/hexane to 5% methanol/ethyl acetate to give, after recrystallizaion from methanol/ethyl acetate, 5-amino-1-(2,4-difluorophenyl)-4-[3-(pyridin-4-yl)benzoyl]pyrazole (0.42 g, Mpt. 218–226° C.).

Example 23

5-Amino-1-(2,4-dimethylphenyl)-4-[3-(pyridin-3-yl)
benzoylpyrazole HCl Salt (69)

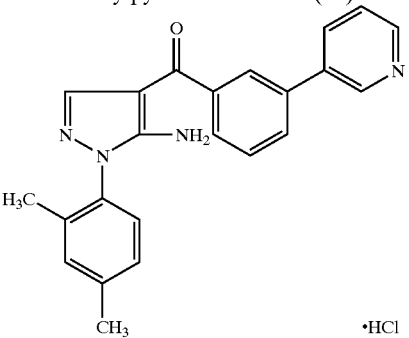

Step 1

Into a solution of n-butyl lithium (165 ml, 264 mmol) in butyl ether (250 ml) at −78 degrees under nitrogen was added 3-bromopyridine (25.4 ml, 264 mmol). After 1 h, added diethylmethoxyborane (52 ml, 396 mmol). The mixture was allowed to warm to room temperature. After 16 h, added water and brine, separated organic layer, dried over sodium sulfate, then concentrated. The resulting slurry was dissolved in isopropanol (500 ml), cooled and the product isolated by filtration give diethyl(3-pyridyl)borane (29.8 g).

Step 2

A mixture of diethyl(3-pyridyl)borane (176.4 g, 1.2 mole), methyl-3-iodobenzoate (262 g, 1 mole), potassium phosphate (318.4 g, 1.5 mole) and tetrakistriphenlyphosphine palladium (0) (57.8 g, 0.05 mole) in DMF (1000 ml) was heated at 80 degrees under argon. After 10 h, the mixture was diluted with water and extracted with ethyl acetate. The organic layer was filtered and washed with water. To the organic fraction was added concentrated HCL (65 ml). The organic layer was separated and extracted with aqueous HCl. The combined acid extractions were treated with ethyl acetate, followed by 50% aqueous sodium hydroxide (55 ml). The organic layer was separated, washed with water and saturated sodium bicarbonate solution, then dried over sodium sulfate. The solution was filtered and concentrated to give methyl-3-(pyridin-3-yl)benzoate (145.3 g).

Step 3

To a solution of methyl-3-(pyridin-3-yl)benzoate (126.2 g, 0.59 mole) in THF (600 ml) was added acetonitrile (37 ml, 0.71 mole) and the reaction was cooled to −40 degrees. A solution of lithium diisopropyl amide (590 ml, 1.18 mole) was added dropwise. After 30 minutes, added methanol (25 ml) and after another 30 minutes, added water (110 ml). Allowed the reaction mixture to warm to 10 degrees and added ethyl acetate. The layers were separated and the aqueous layer was acidified with 1 M HCl. The aqueous layer was extracted with ethyl acetate, diluted with hexane and washed with brine. The organic phase was concentrated, then combined with N,N'-diphenylformanidine (120 g, 0.61 mole) in 800 ml of ethyl acetate. The mixture was stirred at room temperature. After 3 days, the product was collected by filtration and recrystallized from isopropanol, hexane to give 2-(3-pyridin-3-yl)phenyl-3-phenylacrylonitrile (100 g).

Step 4

A solution of 2-(3-pyridin-3-ylphenyl)-3-phenylacrylonitrile (1.0 g, 3 mmol) and 2,4-dimethyphenylhydrazine (0.4 g, 3 mmol) in ethanol (30 ml) was heated at reflux, under nitrogen. After 6 h, the reaction was cooled to room temperature, concentrated to dryness and the residue purified by flash column chromatography (elution gradient: 40–100% ethyl acetate/hexane to 10% methanol/ethyl acetate). The purified residue was taken up in ethyl acetate and HCl/ether added to prepare the salt. After recrystallization from methanol/ethyl acetate was isolated 5-amino-1-(2,4-dimethylphenyl)-4-[3-(pyridin-3-yl)benzoylpryrazole hydrochloride salt (0.74 g, m.pt. 250.7–251.8).

Proceeding as above in Example 23, but replacing 2,4-dimethylphenylhydrazine in step 4 with:

phenylhydrazine,
2-methyl-4-chlorophenylhydrazine;
4-methoxyphenylhydrazine;
4-methylsulfonylphenylhydrazine;
2-ethylphenylhydrazine;
4-isopropylphenylhydrazine;
2-methoxyphenylhydrazine;
3-chloro-4-methylphenylhydrazine,
3-fluorophenylhydrazine, and
3-fluoro-6-methylphenylhydrazine respectively, the following compounds were obtained.

| Mole Structure | CPD # | HRMS MW |
|---|---|---|
| | 139 | 376.845 |
| | 73 | 425.317 |
| | 140 | 406.871 |
| | 75 | 454.936 |
| | 76 | 404.899 |

-continued

| Mole Structure | CPD # | HRMS MW |
|---|---|---|
| | 141 | 418.926 |
| | 142 | 406.871 |
| | 143 | 425.317 |
| | 144 | 394.835 |

-continued

| Mole Structure | CPD # | HRMS MW |
|---|---|---|
| | 145 | 408.862 |

Example 24

5-Amino-1-(4-fluorophenyl)-4-[3-{2(R),3-dihydroxypropoxy}benzoyl]pyrazole (106)

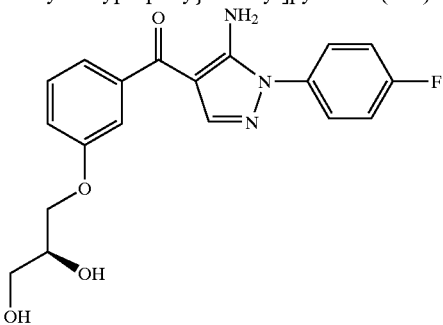

Step 1

To a solution of 5-amino-4-(3-hydroxybenzoyl)-1-(4-fluorophenyl)pyrazole (0.5 g, 1.68 mmol) in 5 ml dry dimethylformamide was added D-α,β-isopropylideneglycerol-γ-tosylate (0.72 g, 2.52 mmol) followed by anhydrous potassium carbonate (0.695 g, 5.04 mmol). The reaction was warmed to 80° C. under argon. After 24 hours, the reaction was cooled to room temperature and an additional 500 mg of D-α,β-isopropylideneglycerol-γ-tosylate was added and the reaction was warmed back to 80° C. under argon. After 8 additional hours, the reaction was cooled to room temperature and diluted with distilled water (50 ml) and the product was extracted into ether. The combined organics were washed with brine (50 ml), dried over MgSO$_4$ and then concentrated in vacuo to a yellow oil. The oil was purified by flash column chromatography on silica gel using 2:1–1:1 hexanes/ethyl acetate as eluent. Concentration of the column fractions in vacuo gave 556 mg of the desired acetal.

Step 2

To a solution of the acetal formed above (0.556 g, 1.35 mmol) in methanol (10 ml) was added distilled water (2 ml) and p-toluenesulfonic acid monohydrate (5 mg). The solution was warmed to 80° C. under an argon atmosphere. After 2 h, the reaction mixture was cooled to room temperature concentrated in vacuo to a yellow oil which was redissolved in ethyl acetate (50 ml) and saturated sodium bicarbonate (50 ml). The organic layer was separated, dried over MgSO$_4$ and then concentrated in vacuo to a white solid. Recrystallization from hexanes/ethyl acetate gave 196 mg of the desired diol (Mpt. 150.2–153.0° C.).

Example 25

5-Amino-1-(4-fluorophenyl)-4-thenoyl-pyrazole (114)

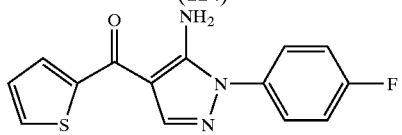

Proceeding as described in Example 1, step 2, but replacing 2-(3-bromobenzoyl)acetonitrile with 2-(2-thenoyl)acetonitrile and then following step 3 was obtained 5-amino-1-(4-fluorophenyl)-4-(2-thenoyl)-pyrazole.

Proceeding as described in Example 1, step 2, but replacing 2-(3-bromobenzoyl)acetonitrile with 2-(2-furanoyl)acetonitrile and then following step 3 was obtained 5-amino-1-(4-fluorophenyl)-4-(2-furanoyl)-pyrazole (115).

Proceeding as described in Example 1, step 2, but replacing 2-(3-bromobenzoyl)acetonitrile with 2-(2-methyl-3-furanoyl)acetonitrile and substituting 4-fluorophenylhydrazine in step 3 with 2,4-difluorophenylhydrazine was obtained 5-amino-1-(2,4-difluorophenyl)-4-(2-methylfuran-3-oyl)-pyrazole (116).

Proceeding as described in Example 1, step 2, but replacing 2-(3-bromobenzoyl)acetonitrile with 2-(6-quinolinoyl)acetonitrile and substituting 4-fluorophenylhydrazine in step 3 with 2,4-difluorophenylhydrazine was obtained 5-amino-1-(2,4-difluorophenyl)-4-(6-quinolinoyl)-pyrazole.HCl (117) (mpt. 220–259.2).

Example 26

The following are representative pharmaceutical formulations containing a compound of Formula (I).

Tablet Formulation

The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable formulation.

| Ingredient | Amount |
|---|---|
| compound of this invention | 0.2 g |
| sodium acetate buffer solution, 0.4 M | 2.0 ml |
| HCl (1 N) or NaOH (1 N) | q.s. to suitable pH |
| water (distilled, sterile) | q.s. to 20 ml |

All of the above ingredients, except water, are combined and heated to 60–70° C. with stirring. A sufficient quantity of water at 60° C. is then added with vigorous stirring to emulsify the ingredients, and water then added q.s. to 100 g.

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| compound of the invention | 500 mg |
|---|---|
| Witepsol ® H-15 | balance |

Example 27

Inhibition Of p-38 (MAP) Kinase . . . In Vitro Assay

The p-38 MAP kinase inhibitory activity of compounds of this invention in vitro was determined by measuring the transfer of the γ-phosphate from γ-$^{33}$P-ATP by p-38 kinase to Myelin Basic Protein (MBP), using the a minor modification of the method described in Ahn, N. G.; et al. *J. Biol. Chem.* Vol. 266(7), 4220–4227, (1991).

The phosphorylated form of the recombinant p38 MAP kinase was expressed with SEK-1 and MEKK in *E. Coli* and then purified by affinity chromatography using a Nickel column.

The phosphorylated p38 MAP kinase was diluted in kinase buffer (20 mM 3-(N-morpholino)propanesulfonic acid, pH 7.2, 25 mM β-glycerol phosphate, 5 mM ethylene glycol-bis(beta-aminoethyl ether)-N,N,N',N'-tetraacetic acid, 1 mM sodium vanadate, 1 mM dithiothreitol, 40 mM magnesium chloride). Test compound dissolved in DMSO or only DMSO (control) was added and the samples were incubated for 10 min at 30° C. The kinase reaction was initiated by the addition of a substrate cocktail containing MBP and γ-$^{33}$P-ATP. After incubating for an additional 20 min at 30° C., the reaction was terminated by adding 0.75% phosphoric acid. The phosphorylated MBP was then separated from the residual γ-$^{33}$P-ATP using a phosphocellulose membrane (Millipore, Bedford, Mass.) and quantitated using a scintillation counter (Packard, Meriden, Conn.).

Compounds of the invention wer active in this assay. The p-38 inhibitory activities (expressed as $IC_{50}$, the concentration causing 50% inhibition of the p-38 enzyme being assayed) of some compounds of the invention are:

| CPD # | $IC_{50}$, μM | CPD # | $IC_{50}$, μM |
|---|---|---|---|
| 1 | 1.81 | 19 | 1.45 |
| 2 | 3.29 | 21 | 2.18 |
| 3 | 1.78 | 27 | 2.72 |
| 4 | 6.18 | 33 | 1.12 |
| 6 | 1.74 | 38 | 6.31 |
| 9 | 1.32 | 43 | 6.52 |
| 14 | 1.27 | 50 | 1.25 |

Example 28

Inhibition of LPS-Induced TNF-α Production In THP1 Cells . . . In Vitro Assay

The ability of the compounds of this invention to inhibit the TNF-α release was determined using a minor modification of the methods described in Blifeld, C. et al. *Transplantation*, Vol. 51(2), 498–503, (1991).

(a) Induction of TNF Biosynthesis

THP-1 cells were suspended in culture medium [RPMI (Gibco-BRL, Gailthersburg, Md.) containing 15% fetal bovine serum, 0.02 mM 2-mercaptoethanol], at a concentration of 2.5×10$^6$ cells/ml and then plated in 96 well plate (0.2 ml aliquots in each well). Test compounds were dissolved in DMSO and then diluted with the culture medium such that the final DMSO concentration was 5%. 20 μl aliquots of test solution or only medium with DMSO (control) were added to each well. The cells were incubated for 30 min., at 37° C. LPS (Sigma, St. Louis, Mo.) was added to the wells at a final concentration of 0.5 μg/ml, and cells were incubated for an additional 2 h. At the end of the incubation period, culture supernatants were collected and the amount of TNF-α present was determined using an ELISA assay as described below.

(b) ELISA Assay

The amount of human TNF-α present was determined by a specific trapping ELISA assay using two anti-TNF-α antibodies (2TNF-H22 and 2TNF-H34) described in Reimund, J. M., et al. *GUT.* Vol. 39(5),684–689 (1996).

Polystyrene 96-well plates were coated with 50 μl per well of antibody 2TNF-H22 in PBS (10 μg/ml) and incubated in a humidified chamber at 4° C. overnight. The plates were washed with PBS and then blocked with 5% nonfat-dry milk in PBS for 1 hour at room temperature and washed with 0.1% BSA (bovine serum albumin) in PBS.

TNF standards were prepared from a stock solution of human recombinant TNF-α (R&D Systems, Minneapolis, Minn.). The concentration of the standards in the assay began at 10 ng/ml followed by 6 half log serial dilution's.

25 μl aliquots of the above culture supernatants or TNF standards or only medium (control) were mixed with 25 μl aliquots of biotinylated monoclonal antibody 2TNF-H34 (2 μg/ml in PBS containing 0.1% BSA) and then added to each well. The samples were incubated for 2 h at room temperature with gentle shaking and then washed 3 times with 0.1% BSA in PBS. 50 μl of peroxidase-streptavidin (Zymed, S. San Francisco, Calif.) solution containing 0.416 μg/ml of peroxidase-streptavidin and 0.1% BSA in PBS was added to each well. The samples were incubated for an additional 1 h at room temperature and then washed 4 times with 0.1% BSA in PBS. 50 μl of O-phenylenediamine solution (1 μg/ml O-phenylene-diamine and 0.03% hydrogen peroxide in 0.2M citrate buffer pH 4.5) was added to each well and the samples were incubated in the dark for 30 min., at room temperature. Optical density of the sample and the reference were read at 450 nm and 650 nm, respectively. TNF-α levels were determined from a graph relating the optical density at 450 nm to the concentration used.

The $IC_{50}$ value was defined as the concentration of the test compound corresponding to half-maximal reduction in 450 nm absorbance. Compounds of the invention were active in this assay. The activity of selected compounds is shown below.

| CPD # | $IC_{50}$, μM | CPD # | $IC_{50}$, μM |
|---|---|---|---|
| 1 | 1.77 | 21 | 0.61 |
| 2 | 6.30 | 27 | 0.83 |
| 4 | 1.26 | 33 | 0.14 |
| 6 | 1.04 | 38 | 0.69 |
| 10 | 1.62 | 43 | 0.17 |
| 13 | 0.77 | 50 | 0.51 |
| 19 | 0.17 | | |

Example 29

Inhibition of LPS-Induced TNF-α Production In Rats . . . In Vivo Assay

The ability of the compounds of this invention to inhibit the TNF-α release, in vivo, was determined using a minor modification of the methods described in described in Zanetti, G.; Heumann, D., et al., "Cytokine production after intravenous or peritoneal Gram-negative bacterial challenge in mice," *J. Immunol.*, 148, 1890, (1992) and Sekut, L., Menius, J. A., et. al., "Evaluation of the significance of elevated levels of systemic and localized tumor necrosis factor in different animal models of inflammation," *J. Lab. Clin. Med.*, 124, 813, (1994).

Female Sprague-Dawley rats weighing 110–140 grams (Charles River, Hollister, Calif.) were acclimated for one week. Groups containing 8 mice each were dosed orally either with the test compounds dissolved in an aqueous vehicle containing 0.9% sodium chloride, 0.5% sodium carboxymethyl-cellulose, 0.4% polysorbate 80, 0.9% benzyl alcohol (CMC vehicle) or only vehicle (control group). After 30 min., the mice were injected intraperitoneally with 50 μg/kg of LPS (Sigma, St. Louis, Mo.). After 1.5 h, the mice were sacrificed by $CO_2$ inhalation and blood was harvested by cardiocentesis. Blood was clarified by centrifugation at 15,600×g for 5 min., and sera were transferred to clean tubes and frozen at −20° C. until analyzed for TNF-α by ELISA assay (Biosource International, Camarillo, Calif.) following the manufacturer's protocol.

The TNF-α inhibitory activity of selected compounds of the invention, i.e., the measure of the TNF-α content in the test group relative to the vehicle treated group (control group) at 30 mg was:

| CPD # | % Inhibition | CPD # | % Inhibition |
|---|---|---|---|
| 3 | 96 | 19 | 76 |
| 8 | 86 | 34 | 75 |
| 16 | 86 | | |

Example 30

Adjuvant Arthritis Assay In Rats . . . In Vivo Assay

The Anti-inflammatory activity of the compounds of this invention was determined utilizing adjuvant induced arthritis in rats. Briefly, Female Sprague Dawley rats, weighing 120–155 g (Charles River, Hollister, Calif.) were acclimated in-house for approximately 1 week prior to use. On day 1, the animals were injected intradermally in the 1/4 proximal portion of the tail with 0.1 ml of a mineral oil (Sigma, St. Louis, Mo.) suspension of heat killed and dried *Mycobacterium Butyricum* (Difco, Bacto., Des., Lot 115979JA/EXP9/99) at a concentration of 1 mg/0.1 ml.

On day 7, the test compounds were administered in CMC vehicle through to day 18. On day 18, following the administration of the compound, animals were weighed. Clinical scores were obtained to evaluate the intensity of edema in the four paws and tail. A score of 0 to 4 was assigned to each paw and 0 to 3 to the tail such that the maximum score was 19. Polyarthritic animals were scored 0 when no inflammatory signs (swelling and redness) were observed in any of the small joints (intraphalangeal, metacarpophalangeal, metatarsophalangeal) or large joints (wrist/carpus, ankle/tarsus). Animals were scored 1 when slight inflammation was observed, 2 moderate edema, 3 severe edema, and 4 when very severe edema was present. The tail was scored 0 when no signs of edema or necrotic tissue was observed, 1 when inocula injection sites and immediate surrounding tissue exhibit slight edema, 2 when approximately 1/4 of the tail was either inflamed or exhibiting necrotic tissue, and 3 when over 1/4 of the tail exhibited severe necroses or edema. Following clinical scores, the hind paws were transected at the distal tibia, just proximal to the tarsal joint. The left and right hind paws were weighed individually, and recorded.

The compounds of the present invention exhibit anti-inflammatory activity when tested in this assay.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound selected from the group of compounds represented by Formula (I):

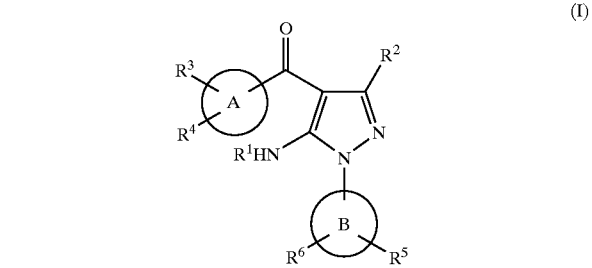

wherein:
$R^1$ is hydrogen or acyl;
$R^2$ is hydrogen or alkyl;
A and B are simultaneously an aryl or a heteroaryl ring;
$R^3$ is selected from the group consisting of:
  (a) optionally substituted heterocyclyl;
  (b) heteroalkenyl;
  (c) heteroalkynyl;
  (d) optionally substituted heterocyclylalkyl;
  (e) optionally substituted heterocyclylalkenyl;
  (f) optionally substituted heterocyclylalkynyl;
  (g) optionally substituted heterocyclylalkoxy, cyclyloxy or heterocyclyloxy;
  (h) optionally substituted heterocyclylalkylamino;
  (i) optionally substituted heterocyclylalkylcarbonyl;
  (j) —Y-(alkylene)-$R^9$ where:
    Y is a single bond, —O—, —NH— or —S(O)$_n$— (where n is an integer from 0 to 2); and
    $R^9$ is cyano, optionally substituted heteroaryl, —COOH, —COR$^{10}$, —CONR$^{12}$R$^{13}$, —SO$_2$R$^{14}$, —SO$_2$NR$^{15}$R$^{16}$, —NHSO$_2$R$^{17}$ or —NHSO$_2$NR$^{18}$R$^{19}$, where $R^{10}$ is optionally substituted heterocyclic, and $R^{12}$, $R^{13}$, $R^{14}$, $R^{15}$, $R^{16}$, $R^{17}$, $R^{18}$ and $R^{19}$ are, independently of each other, hydrogen, alkyl or heteroalkyl;
  (k) —C(=NR$^{20}$)(NR$^{21}$R$^{22}$) where $R^{20}$, $R^{21}$ and $R^{22}$ independently represent hydrogen, alkyl or hydroxy, or $R^{20}$ and $R^{21}$ together are —(CH$_2$)$_n$— where n is 2 or 3 and $R^{22}$ is hydrogen or alkyl;
  (l) —NHC(X)NR$^{23}$R$^{24}$ where X is —O— or —S—, and $R^{23}$ and $R^{24}$ are, independently of each other, hydrogen, alkyl or heteroalkyl;
  (m) —CONR$^{25}$R$^{26}$ where $R^{25}$ and $R^{26}$ independently represent hydrogen, alkyl, heteroalkyl or optionally substituted heterocyclylalkyl, or $R^{25}$ and $R^{26}$ together with the nitrogen to which they are attached form an optionally substituted heterocyclyl ring;
  (n) cycloalkylalkyl and cycloalkylalkynyl, all optionally substituted with alkyl, halo, hydroxy or amino;
  (o) arylaminoalkylene or heteroarylaminoalkylene;
  (p) Z-alkylene-NR$^{30}$R$^{31}$ or Z-alkylene-OR$^{32}$ where Z is —O—, and $R^{30}$, $R^{31}$ and $R^{32}$ are independently of each other, hydrogen, alkyl or heteroalkyl;
  (q) —OC(O)-alkylene-CO$_2$H or —OC(O)—NR'R" (where R' and R" are independently hydrogen or alkyl);
  (r) heteroarylalkenylene or heteroarylalkynylene; and
  (s) heteroalkylamino;
$R^4$ is selected from the group consisting of:
  (a) hydrogen;
  (b) halo;
  (c) alkyl;
  (d) alkoxy; and
  (e) hydroxy;

$R^5$ is selected from the group consisting of:
(a) hydrogen;
(b) halo;
(c) alkyl;
(d) haloalkyl;
(e) thioalkyl;
(f) hydroxy;
(g) amino;
(h) alkylamino;
(i) dialkylamino;
(j) heteroalkyl;
(k) optionally substituted heterocycle;
(l) optionally substituted heterocyclylalkyl;
(m) optionally substituted heterocyclylalkoxy;
(n) alkylsulfonyl;
(o) aminosulfonyl, mono-alkylaminosulfonyl or di-alkylaminosulfonyl;
(p) heteroalkoxy; and
(q) carboxy;
$R^6$ is selected from the group consisting of:
(a) hydrogen;
(b) halo;
(c) alkyl; and
(d) alkoxy; and
prodrugs, individual isomers, mixtures of isomers and pharmaceutically acceptable salts thereof.

2. The compound of claim 1 wherein $R^3$ is:
(a) optionally substituted heterocyclyl;
(b) heteroalkenyl;
(c) heteroalkylamino;
(d) optionally substituted heterocyclylalkyl or heterocyclyloxy;
(e) optionally substituted heterocyclylalkenyl;
(f) optionally substituted heterocyclylalkynyl;
(g) optionally substituted heterocyclylalkoxy;
(h) optionally substituted heterocyclylalkylamino;
(i) optionally substituted heterocyclylalkylcarbonyl;
(l) —Y—(alkylene)-$R^9$ where Y is a single bond —O— or —NH— and $R^9$ is optionally substituted heteroaryl, —CONR$^{12}$R$^{13}$, SO$_2$R$^{14}$, —SO$_2$NR$^{15}$R$^{16}$ —NHSO$_2$R$^{17}$ or —NHSO$_2$NR$^{18}$R$^{19}$ where $R^{12}$, $R^{13}$, $R^{14}$, $R^{15}$, $R^{16}R^{17}$, $R^{18}$ and $R^{19}$ are independently of each other hydrogen, alkyl or heteroalkyl,
(m) cycloalkylalkyl, and cycloalkylalkynyl, all optionally substituted with alkyl, halo, hydroxy or amino;
(n) arylaminoalkylene or heteroarylaminoalkylene; or
(o) Z-alkylene-NR$^{30}$R$^{31}$ where Z is —O—, and $R^{30}$ and $R^{31}$ are independently of each other, hydrogen, alkyl or heteroalkyl.

3. The compound of claim 2 wherein $R^1$ and $R^2$ are hydrogen; and B is phenyl.

4. The compound of claim 3 wherein A is phenyl.

5. The compound of claim 4 wherein $R^4$ is hydrogen; and $R^5$ is halo or alkyl.

6. The compound of claim 5 wherein $R^5$ is chloro, fluoro or methyl; and $R^6$ is hydrogen, chloro, fluoro, methyl or methoxy.

7. The compound of claim 6, wherein $R^3$ is at the 3-position.

8. The compound of claim 7, wherein $R^5$ is 4-F and $R^6$ is hydrogen.

9. The compound of claim 7, wherein $R^5$ is 2-Me and $R^6$ is hydrogen.

10. A compound selected from the group of compounds represented by the Formula:

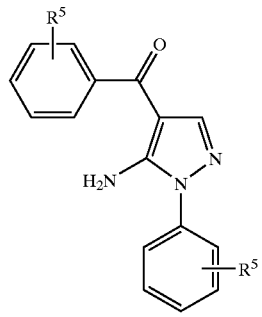

wherein:
$R^5$ is halo or alkyl; and
$R^3$ is:
(a) heteroalkylamino;
(b) optionally substituted heterocyclylalkyl;
(c) optionally substituted heterocyclylalkoxy;
(d) optionally substituted heterocyclylalkylamino;
(e) —Y—(alkylene)-$R^9$ where Y is a single bond —O— or —NH— and $R^9$ is optionally substituted heteroaryl, —CONR$^{12}$R$^{13}$, SO$_2$R$^{14}$, —SO$_2$NR$^{15}$R$^{16}$—NHSO$_2$R$^{17}$ or —NHSO$_2$NR$^{18}$R$^{19}$ where $R^{12}$, $R^{13}$, $R^{14}$, $R^{15}$, $R^{16}R^{17}$, $R^{18}$ and $R^{19}$ are independently of each other hydrogen, alkyl or heteroalkyl; or
(f) Z-alkylene-NR$^{30}$R$^{31}$ where Z is —O—, and $R^{30}$ and $R^{31}$ are independently of each other, hydrogen, alkyl or heteroalkyl;
(g) pyridinyl, N-oxidopyridinyl or pyridonyl; or
(h) sulfamoylphenyl, methylsulfonylphenyl, carboxyphenyl or ethoxycarbonylphenyl; and
prodrugs, individual isomers, mixtures of isomers and pharmaceutically acceptable salts thereof.

11. The compound of claim 10, wherein $R^3$ is heteroalkylamino.

12. The compound of claim 11, wherein $R^3$ is at the 3-position and is selected from the group consisting of 2-dimethylaminoethylamino and 3-dimethylaminopropylamino.

13. The compound of claim 10, wherein $R^3$ is optionally substituted heterocyclylalkyl, optionally substituted heterocyclylalkoxy or optionally substituted heterocyclylalkylamino.

14. The compound of claim 13, wherein $R^3$ is at the 3-position and is selected from the group consisting of 3-(morpholin-4-yl)propoxy, 2-(morpholin-4-yl)ethoxy, 2-(2-oxo-pyrrolidin-1-yl)ethoxy, 3-(morpholin-4-yl)propyl, 2-(morpholin-4-yl)ethyl, 4-(morpholin-4-yl)butyl, 3-(morpholin-4-yl)propylamino, 2-(morpholin-4-yl)ethylamino, 4-hydroxypiperidinylmethyl, 2-(S,S-dioxo-thiamorpholin-4-yl)ethyl, 3-(S,S-dioxo-thiamorpholin-4-yl)propyl and N-methylpiperazinylmethyl.

15. The compound of claim 10 wherein $R^3$ is —Y—(alkylene)-$R^9$ where Y is a single bond, —O— or —NH— and $R^9$ is optionally substituted heteroaryl, —CONR$^{12}$R$^{13}$, SO$_2$R$^{14}$, —SO$_2$NR$^{15}$R$^{16}$—NHSO$_2$R$^{17}$ or —NHSO$_2$R$^{18}$R$^{19}$ where $R^{12}$, $R^{13}$, $R^{14}$, $R^{15}$, $R^{16}R^{17}$, $R^{18}$ and $R^{19}$ are independently of each other hydrogen, alkyl or heteroalkyl.

16. The compound of claim 15, wherein Y is a single bond and $R^9$ is SO$_2$R$^{14}$ or —SO$_2$NR$^{15}$R$^{16}$.

17. The compound of claim 16, wherein $R^3$ is methylsulfonylethyl or sulfamoylethyl.

18. A pharmaceutical composition comprising a therapeutically effective amount of a compound of claim 1 and a pharmaceutically acceptable excipient.

19. A compound selected from the group of compounds represented by Formula (I):

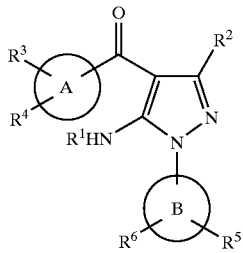

wherein:

A and B are simultaneously an aryl or a heteroaryl ring;

$R^1$ is hydrogen or acyl;

$R^2$ is hydrogen or alkyl;

$R^3$ is:
(a) heteroalkylamino;
(b) optionally substituted heterocyclylalkyl;
(c) optionally substituted heterocyclylalkoxy;
(d) optionally substituted heterocyclylalkylamino;
(e) —Y-(alkylene)-$R^9$ where Y is a single bond, —O— or —NH— and $R^9$ is optionally substituted heteroaryl, —CONR$^{12}$R$^{13}$, SO$_2$R$^{14}$, —SO$_2$NR$^{15}$R$^{16}$—NHSO$_2$R$^{17}$ or —NHSO$_2$NR$^{18}$R$^{19}$ where $R^{12}$, $R^{13}$, $R^{14}$, $R^{15}$, $R^{16}$R$^{17}$, $R^{18}$ and $R^{19}$ are independently of each other hydrogen, alkyl or heteroalkyl; or
(f) Z-alkylene-NR$^{30}$R$^{31}$ where Z is —O—, and $R^{30}$ and $R^{31}$ are independently of each other, hydrogen, or alkyl;
(g) pyridinyl, N-oxidopyridinyl or pyridonyl; or (h) sulfamoylphenyl, methylsulfonylphenyl, carboxyphenyl or ethoxycarbonylphenyl;

$R^4$ is selected from the group consisting of:
(a) hydrogen;
(b) halo;
(c) alkyl;
(d) alkoxy; and
(e) hydroxy;

$R^5$ is selected from the group consisting of:
(a) hydrogen;
(b) halo;
(c) alkyl;
(d) haloalkyl;
(e) thioalkyl;
(f) hydroxy;
(g) amino;
(h) alkylamino;
(i) dialkylamino;
(j) heteroalkyl;
(k) optionally substituted heterocycle;
(l) optionally substituted heterocyclylalkyl;
(m) optionally substituted heterocyclylalkoxy;
(n) alkylsulfonyl;
(o) aminosulfonyl, mono-alkylaminosulfonyl or di-alkylaminosulfonyl;
(p) heteroalkoxy; and
(q) carboxy;

$R^6$ is selected from the group consisting of:
(a) hydrogen;
(b) halo;
(c) alkyl; and
(d) alkoxy; and prodrugs, individual isomers, mixtures of isomers and pharmaceutically acceptable salts thereof.

* * * * *